US012779158B2

(12) United States Patent
Brady et al.

(10) Patent No.: US 12,779,158 B2
(45) Date of Patent: *Nov. 3, 2026

(54) VACUUM SHIELD ASSEMBLY FOR ATTACHMENT TO MEDICAL MASKS

(71) Applicant: SafER Medical Products, LLC, Branson, MO (US)

(72) Inventors: Rob Brady, Sarasota, FL (US); Matt Vergin, St. Petersburg, FL (US); Barry Jennings, Largo, FL (US); Mike Winterhalter, Nokomis, FL (US); Richard Blubaugh, Branson West, MO (US); Craig Randall, Branson, MO (US); Misty Denevan, Branson, MO (US); Todd Baker, Walnut Shade, MO (US); Adriane Marie Jenkel, Bradenton, FL (US); Jeff Nichols, Sarasota, FL (US); Blake Fuller, Sarasota, FL (US); Emanuel Guzman, Sarasota, FL (US)

(73) Assignee: SafER Medical Products, LLC, Branson, MO (US)

( * ) Notice: Subject to any disclaimer, the term of this patent is extended or adjusted under 35 U.S.C. 154(b) by 1224 days.

This patent is subject to a terminal disclaimer.

(21) Appl. No.: 17/716,096

(22) Filed: Apr. 8, 2022

(65) Prior Publication Data

US 2022/0226589 A1 Jul. 21, 2022

Related U.S. Application Data

(63) Continuation-in-part of application No. 17/191,823, filed on Mar. 4, 2021, which is a continuation-in-part (Continued)

(51) Int. Cl.

*A61M 16/00* (2006.01)
*A61M 16/06* (2006.01)

(Continued)

(52) U.S. Cl.

CPC .... *A61M 16/0093* (2014.02); *A61M 16/0009* (2014.02); *A61M 16/06* (2013.01);

(Continued)

(58) Field of Classification Search

None

See application file for complete search history.

(56) References Cited

U.S. PATENT DOCUMENTS

| | | | | |
|---|---|---|---|---|
| 4,794,921 A * | 1/1989 | Lindkvist | A61M 16/0833 | 128/203.29 |
| 4,807,617 A * | 2/1989 | Nesti | A61M 16/06 | 128/203.29 |

(Continued)

FOREIGN PATENT DOCUMENTS

| | | |
|---|---|---|
| CN | 105797246 A | 7/2016 |
| CN | 206007759 U | 3/2017 |
| WO | WO2021207292 | 10/2021 |

OTHER PUBLICATIONS

International Search Report and Written Opinion for PCT/US2021/048141; United States Patent Office; Nov. 17, 2021; entire document.

(Continued)

*Primary Examiner* — Bradley H Philips
(74) *Attorney, Agent, or Firm* — RAY QUINNEY & NEBEKER; Joseph M. Evans

(57) ABSTRACT

A vacuum shield assembly and related vacuum system intended for attachment to an existing medical mask for oxygen delivery, air suction, nebulization, BIPAP, and/or CPAP. The vacuum shield assembly generally comprises a shield body and a retaining assembly. The retaining assembly may attach the vacuum shield assembly to a vacuum tube of the existing mask, which may be connected to a negative pressure vacuum system. The retaining assembly may also be attached to a nebulizer unit or component thereof, or to (Continued)

an oxygen supply tube of a BIPAP or CPAP mask, or a mask configured for oxygen delivery. The shield body may comprise a lower segment, which may comprise a connecting component configured and dimensioned for attachment to, and for a fluid communication, with the retaining assembly. The shield body may be configured and dimensioned to correspond to the geometry of the existing mask.

13 Claims, 31 Drawing Sheets

Related U.S. Application Data of application No. 17/173,724, filed on Feb. 11, 2021, now Pat. No. 12,083,273.

(60) Provisional application No. 63/075,890, filed on Sep. 9, 2020.

(51) Int. Cl.
*A61M 11/06* (2006.01)
*A61M 16/08* (2006.01)

(52) U.S. Cl.
CPC ......... *A61M 11/06* (2013.01); *A61M 16/0683* (2013.01); *A61M 16/0816* (2013.01); *A61M 2209/088* (2013.01)

(56) References Cited

U.S. PATENT DOCUMENTS

| | | | | |
|---|---|---|---|---|
| 5,592,935 | A | 1/1997 | Elstran et al. | |
| 5,676,133 | A | 10/1997 | Hickle | |
| 5,871,011 | A * | 2/1999 | Howell | A61M 16/0093 128/911 |
| 9,757,528 | B2 | 9/2017 | Rubin | |
| 11,052,208 | B2 | 7/2021 | Curran et al. | |
| 12,083,273 | B1 * | 9/2024 | Brady | A61M 16/009 |
| 2002/0045796 | A1 | 4/2002 | O'Connor et al. | |
| 2009/0020128 | A1 | 1/2009 | Metzger et al. | |
| 2010/0229861 | A1 * | 9/2010 | Nashed | A61M 16/0816 128/203.29 |
| 2014/0251333 | A1 * | 9/2014 | Burk | A61M 16/009 128/205.12 |
| 2015/0202473 | A1 | 7/2015 | Curran et al. | |
| 2016/0074268 | A1 | 3/2016 | Breegi et al. | |
| 2018/0085541 | A1 * | 3/2018 | Ye | A61M 16/107 |
| 2020/0038617 | A1 | 2/2020 | Varga et al. | |
| 2021/0307872 | A1 | 10/2021 | Vizulis et al. | |
| 2021/0346624 | A1 * | 11/2021 | Fiorenza | A61M 16/009 |

OTHER PUBLICATIONS

International Search Report and Written Opinion for PCT/US2021/049619; Feb. 28, 2022; United States Patent Office; entire document.

Soverign Medical, Inc.; Exhlo Shield; Product Information Sheet; Online; Apr. 3, 2020; entire document; https://sovmed.com/wp-content/uploads/2020/07/EXHALO-Introduction-Summary-Soverign-medical-ed3.pdf.

* cited by examiner

VACUUM SHIELD ASSEMBLY FOR ATTACHMENT TO MEDICAL MASKS

FIELD OF INVENTION

The present invention relates to attachments to masks for medical procedures.

BACKGROUND

Medical masks may be used for or for nebulizing a patient or used for Non-Invasive Positive Pressure Ventilation (NIPPV), Bi-level Positive Airway Pressure (BIPAP), Bag-Valve-Mask Resuscitator (BVM), Demand-Valve Resuscitator (DVR), or Constant Positive Airway Pressure (CPAP). Of the masks that currently exist, none are believed to provide a truly efficient means for vacuuming air to create negative pressure, or for implementing a nebulizing or positive pressure procedure and at the same time using negative pressure to vacuum exhaled air from the patient. Accordingly, the industry would benefit by providing a vacuum shield assembly for attachment to a medical mask that may be used for vacuuming exhaled air from patient during nebulization, BIPAP, CPAP, or the delivery of oxygen, or to another type of medical mask, including a face mask, a face tent, a Venturi mask, and/or a non-rebreather. Such a vacuum shield assembly would provide the added benefit of at least partially reducing contact to the mask and/or face of the patient, which may help to counter the risk of contagion of airborne illnesses, e.g., influenza, covid-19, etc., providing added protection to medical providers and staff involved in these procedures and in at least partially reducing the development of fomites from exhaled or aerosolized particles or droplets. Additionally, a benefit in the industry would be provided if such a vacuum shield assembly would be disposable as it would further reduce such risk of contagion. An even further benefit would be provided if such a vacuum shield assembly would be sufficiently versatile to be used as a primary and/or a secondary air vacuuming component, and/or a nebulizing component. Yet a further benefit would be realized if this vacuum shield assembly would be provided in different shapes and sizes to correspond to the geometry and size of the underlying face mask.

SUMMARY

The present invention is directed to a vacuum shield assembly intended for attachment to an existing mask. As used herein, an "existing mask" refers to a suction mask, a mask configured for attachment to a nebulizer, BIPAP, CPAP, BVM, DVR or another related mask, including a mask configured for the delivery of oxygen to the patient, that is already disposed on the head and/or face of a patient. Accordingly, the vacuum shield assembly of the present invention may serve as a primary and/or a secondary suction or vacuum mechanism, which in some embodiments may be connected to a negative pressure vacuum. The vacuum shield assembly generally comprises a shield body and a retaining assembly. The retaining assembly may be used to connect the vacuum shield to a vacuum tube connected to a negative pressure vacuum. The retaining assembly may also be attached to a nebulizer unit or component thereof, or to the oxygen supply tube of a BIPAP or CPAP mask. Additionally, the shield body may comprise a lower segment. The shield body may be configured with or without a circular access opening in the convexity of the shield body that will allow a BVM, or DVR to connect to an existing mask by way of the access opening in order to facilitate the vacuuming of exhaled air during said procedures. The lower segment may further define an interior or inside of the shield body and may comprise a connecting portion disposed in fluid communication with the retaining assembly and the vacuum tube. The shield body may be configured and dimensioned to correspond to the geometry of the existing mask. As an example, the shield body may comprise a substantially concave configuration and/or a variety of shapes, including, but not limited to, a substantially triangular or substantially ovoidal shape. However, other shapes of the shield body are possible, which may also to correspond to the shape of the existing mask and/or the shape of the face and/or head of the patient. As such, it is within the scope of the present invention that the vacuum shield assembly according to the present invention at least partially remove exhaled infectious particles, for example, from a patient that has a respiratory illness. As a result, it is contemplated that such increased removal of exhaled infectious particles at least partially reduce the risk of contagion of medical practitioners and staff assisting with these types of procedures and/or the contamination of physical objects in the vicinity (fomites).

Further embodiments of the present invention comprise a system configured to remove exhaled air from a patient wearing a medical masks. In such embodiments, it is contemplated that a portable vacuum unit be provided and connected to a vacuum tube that itself connects to the vacuum shield assembly, i.e., to the shield body, to create a negative pressure on an interior of the shield body and remove exhaled air. The innovative system may be provided with a retaining assembly, if it is desirable to connect to a component of an existing medical mask, or without a retaining assembly, in embodiments where it is desirable to dispose the shield body directly on the face of the patient.

DETAILED DESCRIPTION

Figure 1:
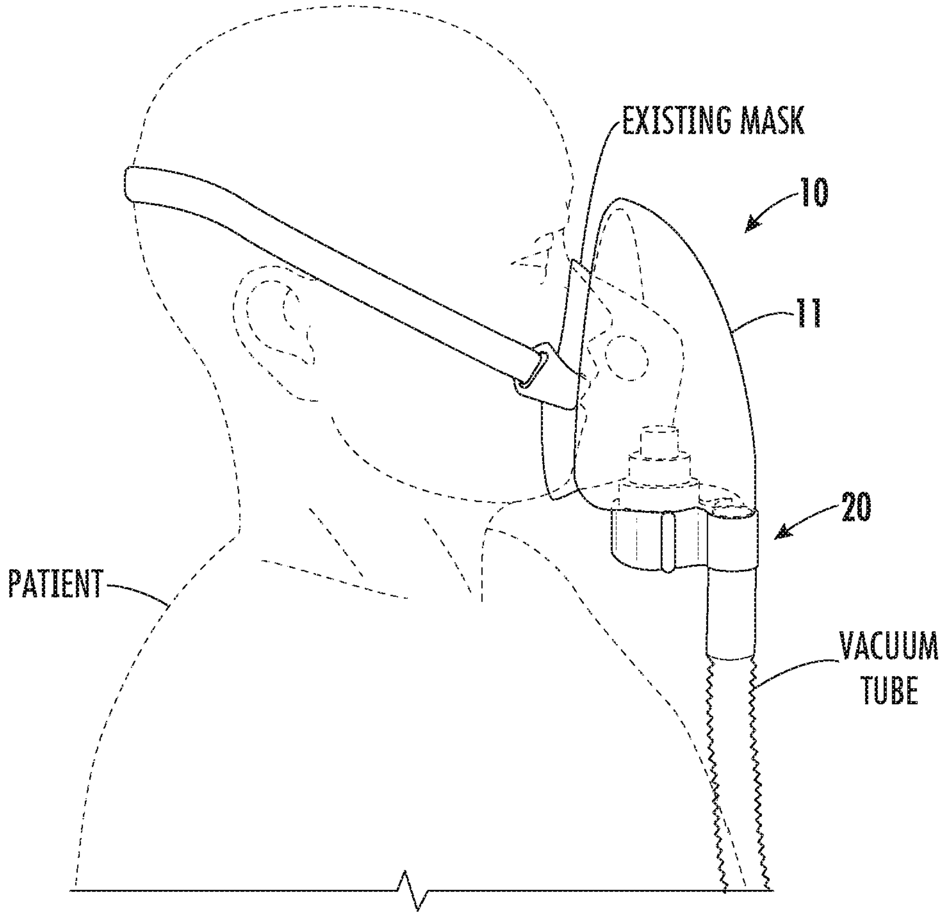
FIG. 1 is a perspective view of one embodiment of the vacuum shield assembly according to the present invention attached to nebulizer mask.
Figure 2:
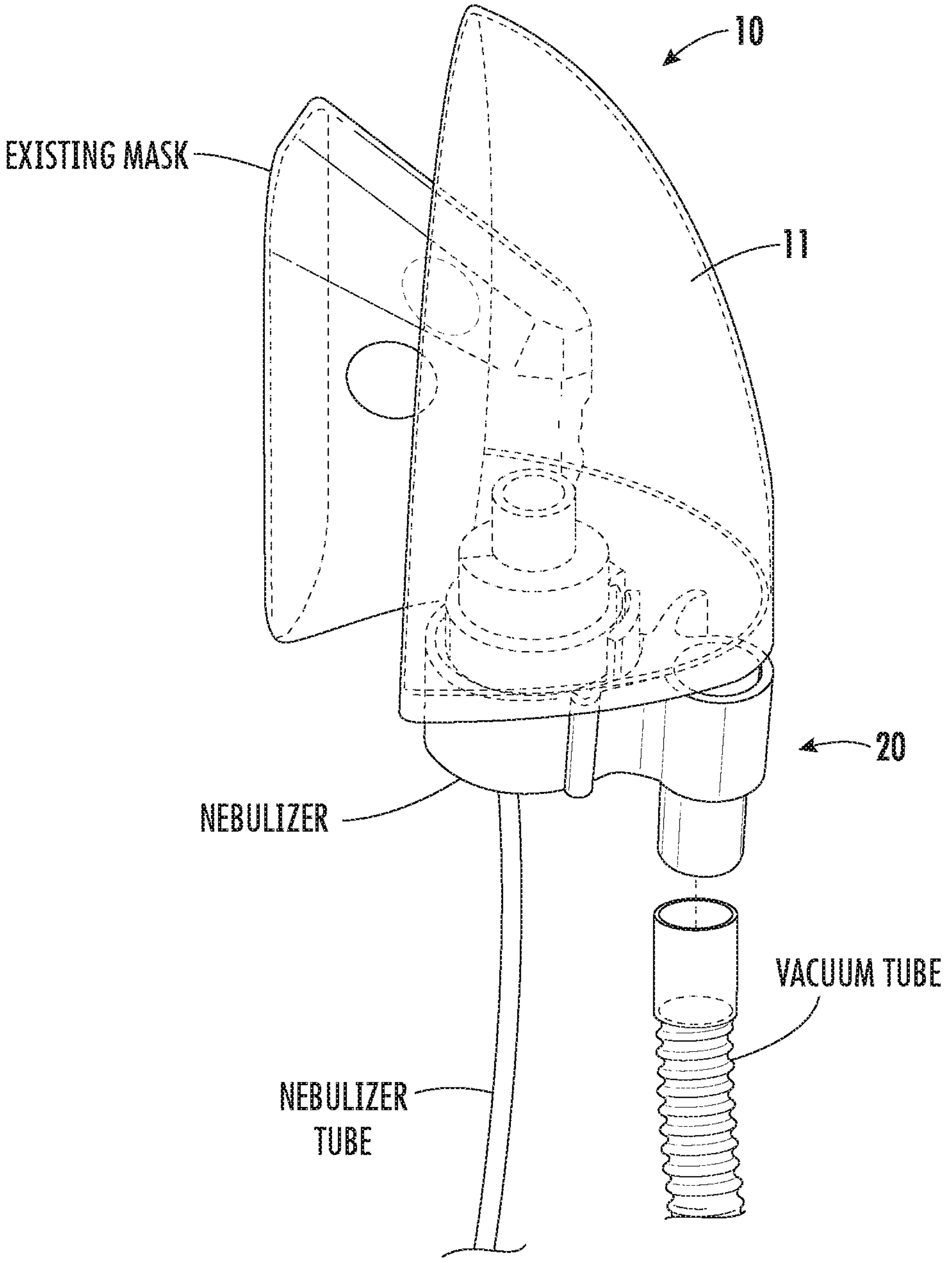
FIG. 2 is a perspective view of another embodiment of the vacuum shield assembly according to the present invention for use with a nebulizer mask.
Figure 3:
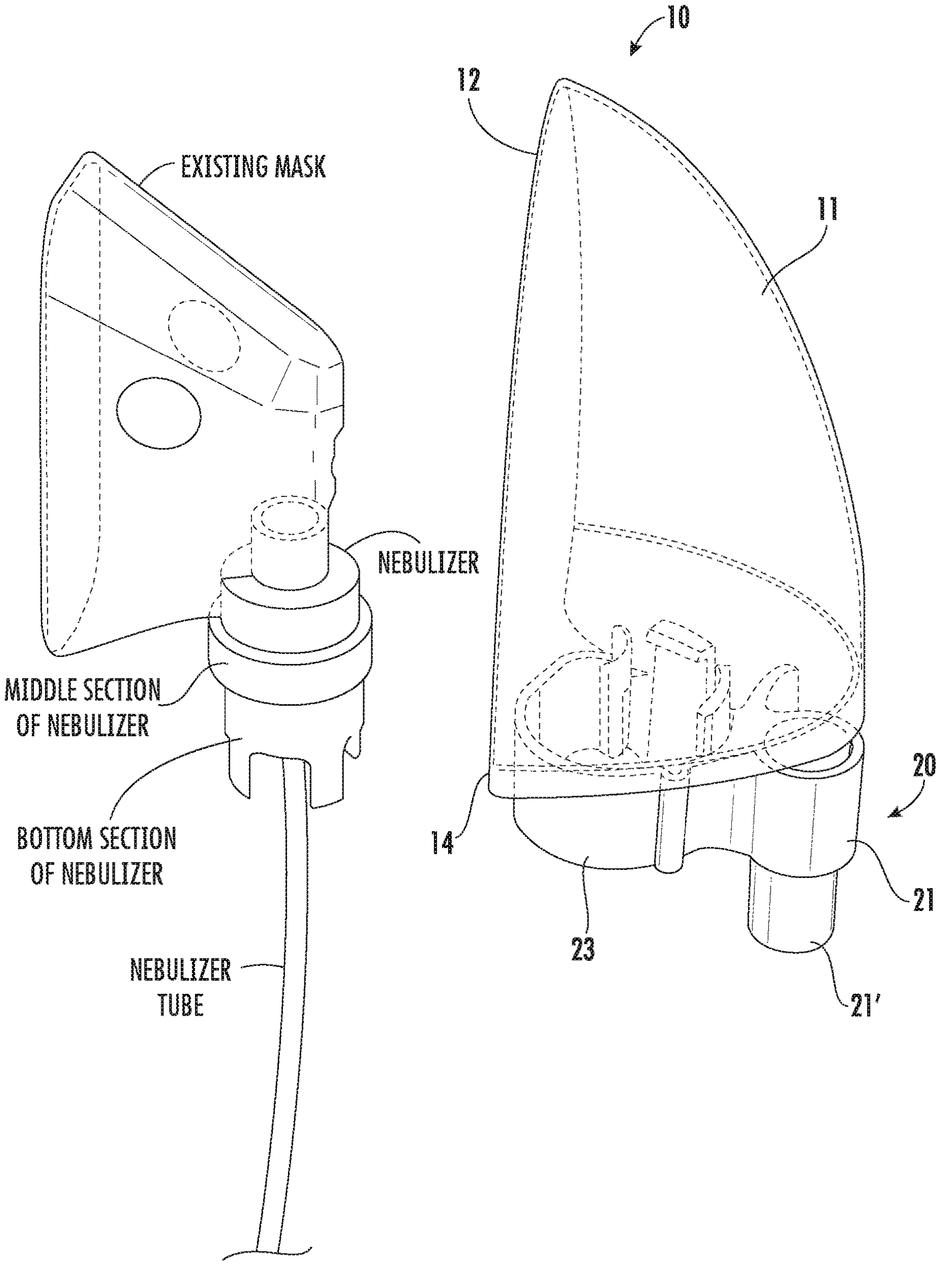
FIG. 3 is a perspective view of yet another embodiment of the vacuum shield assembly according to the present invention for use with a nebulizer mask.
Figure 4:
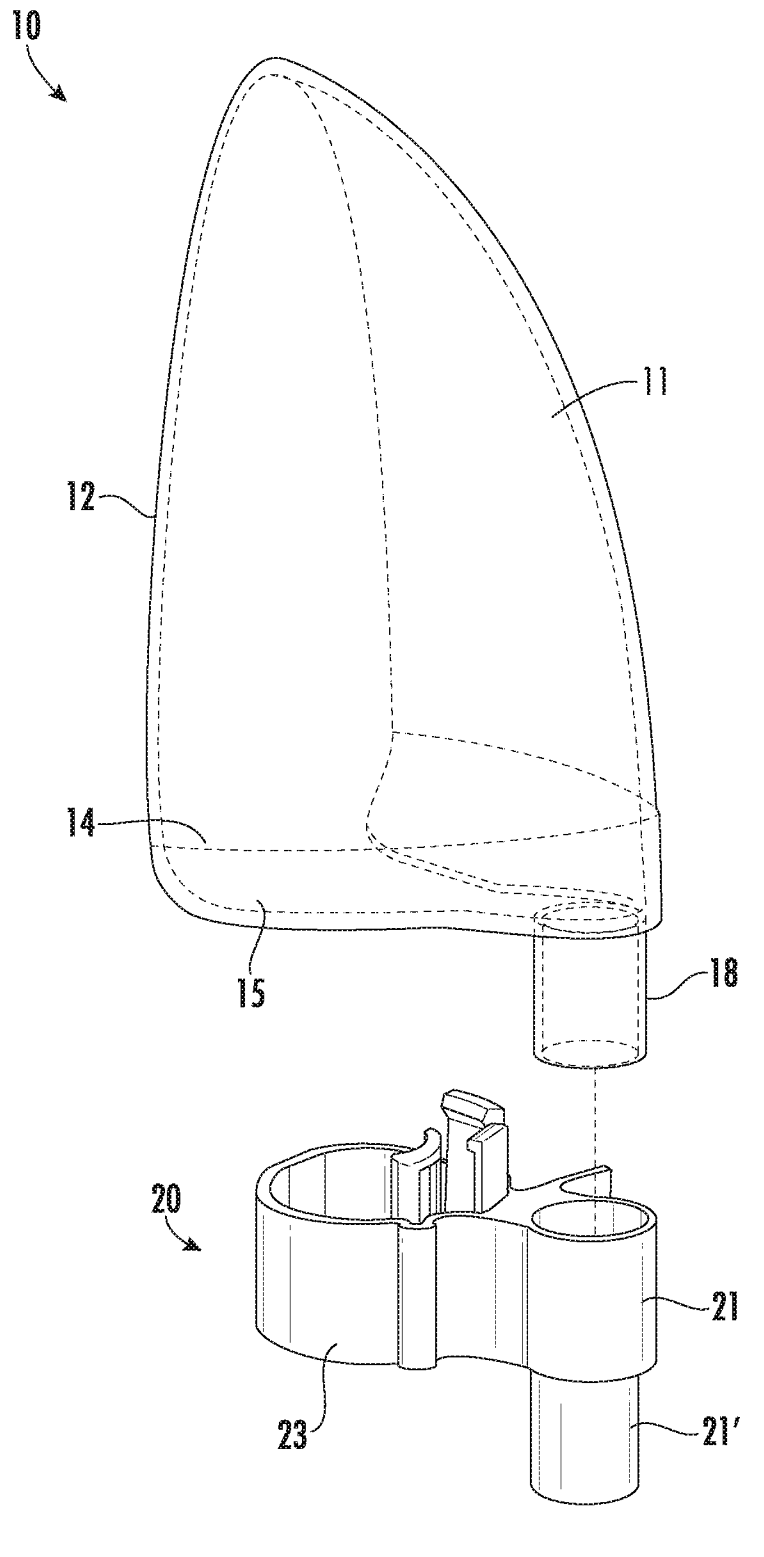
FIG. 4 is a perspective and partially exploded view of a further embodiment of the vacuum shield assembly according to the present invention.
Figure 6:
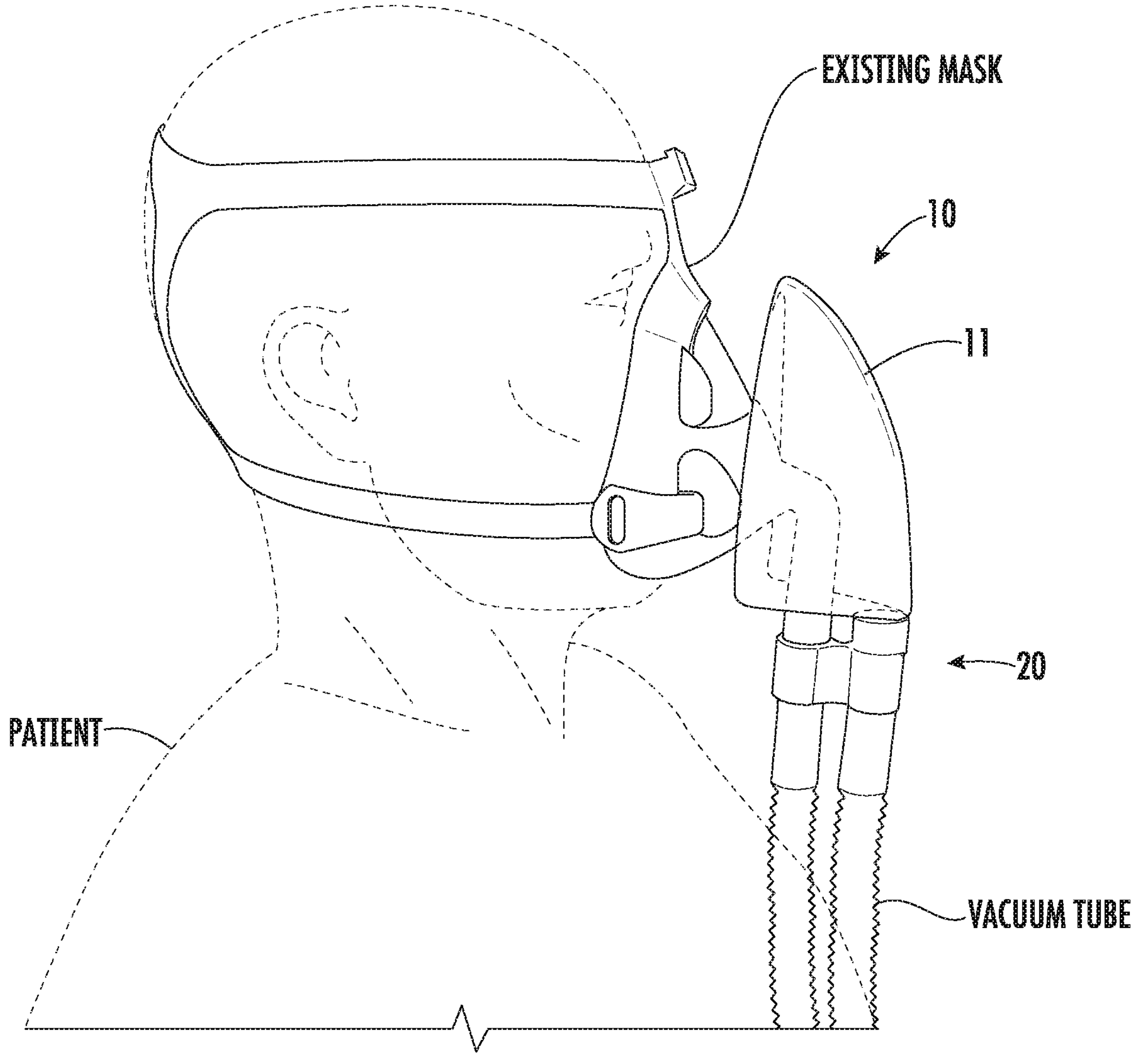
FIG. 6 is a perspective view of one embodiment of the vacuum shield assembly according to the present invention attached to a BIPAP or CPAP mask.
Figure 7:
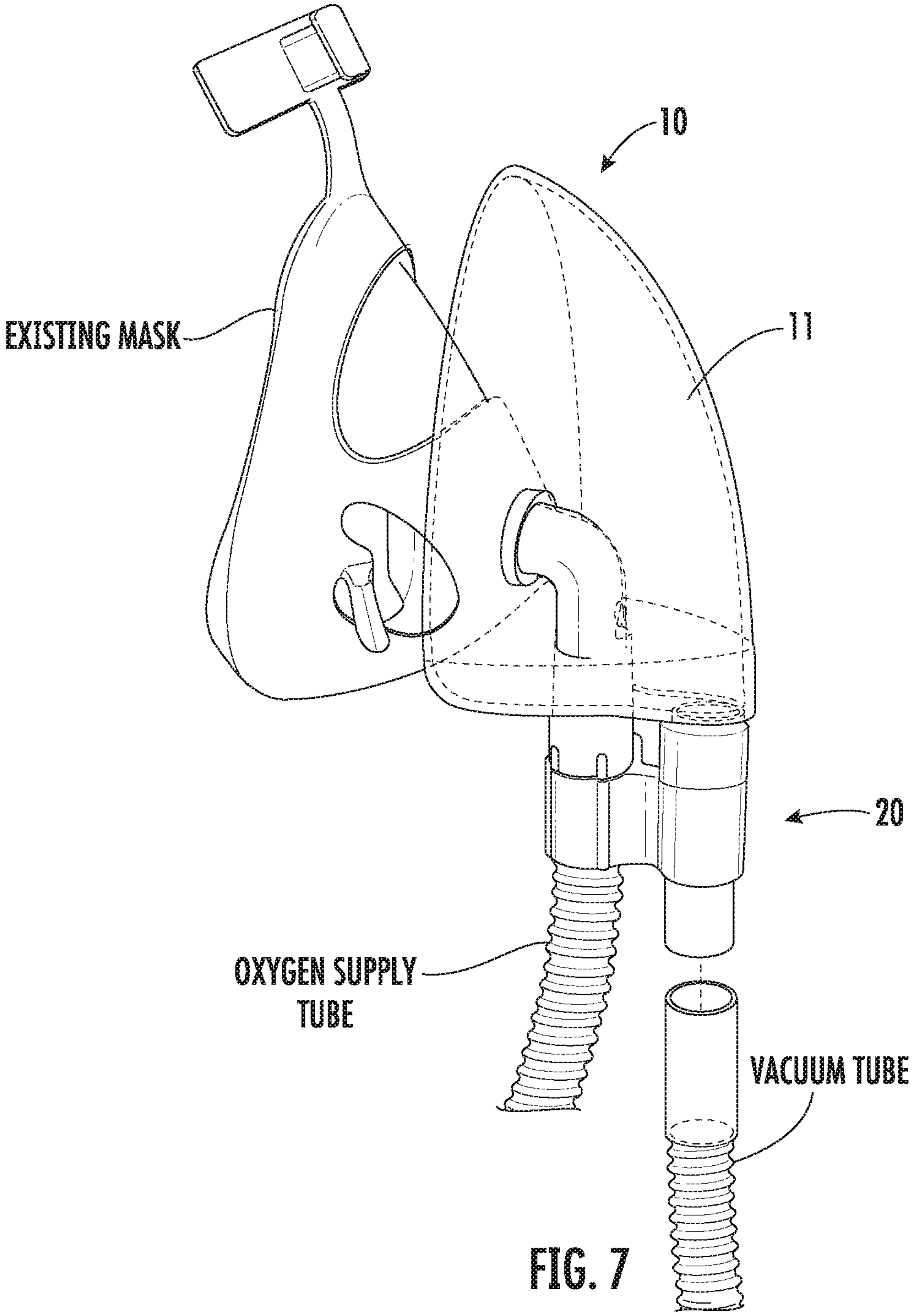
FIG. 7 is a perspective view of another embodiment of the vacuum shield assembly according to the present invention for use with a BIPAP or CPAP mask.
Figure 8:
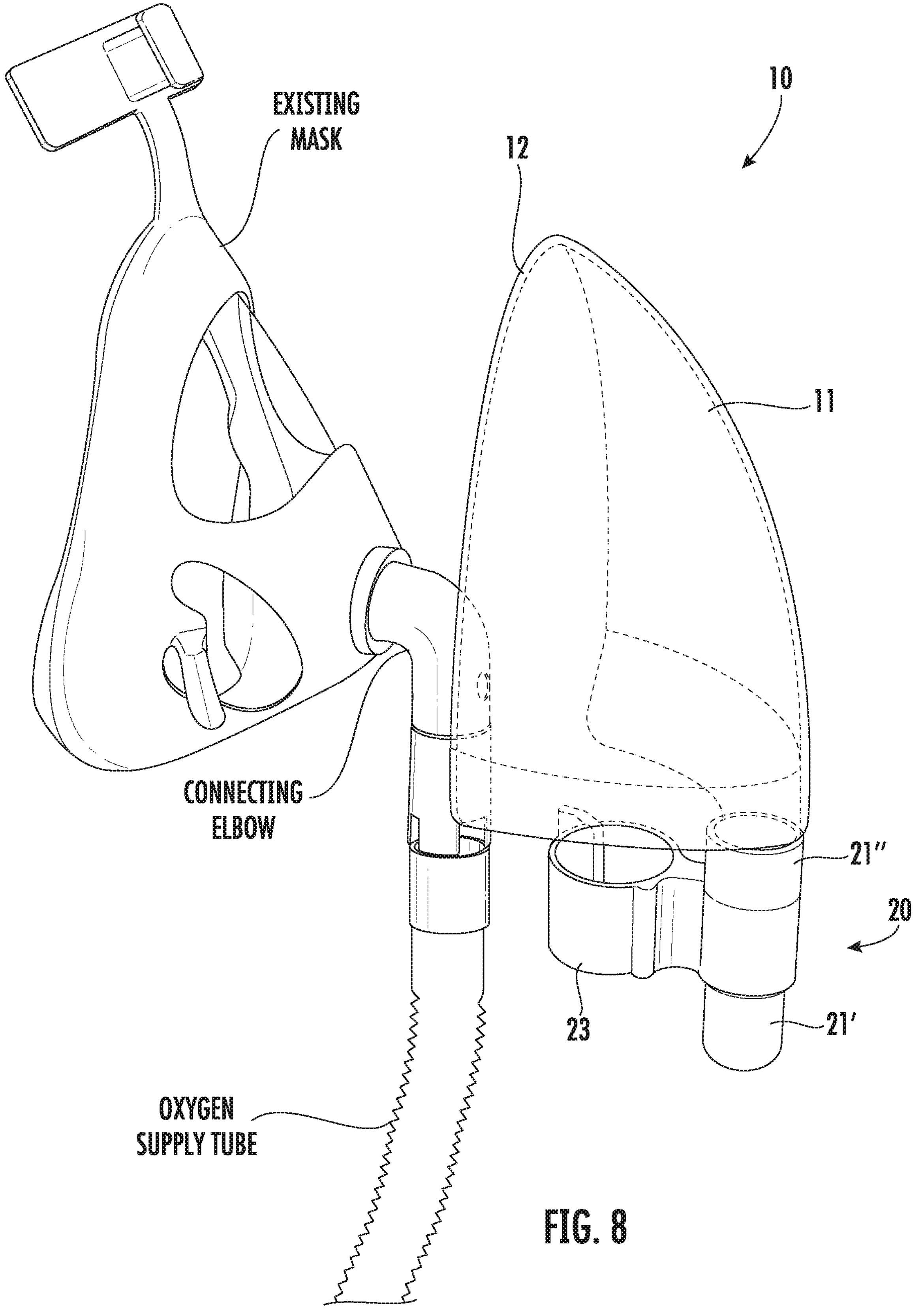
FIG. 8 is a perspective view of yet another embodiment of the vacuum shield assembly according to the present invention for use with a BIPAP or CPAP mask.
Figure 9:
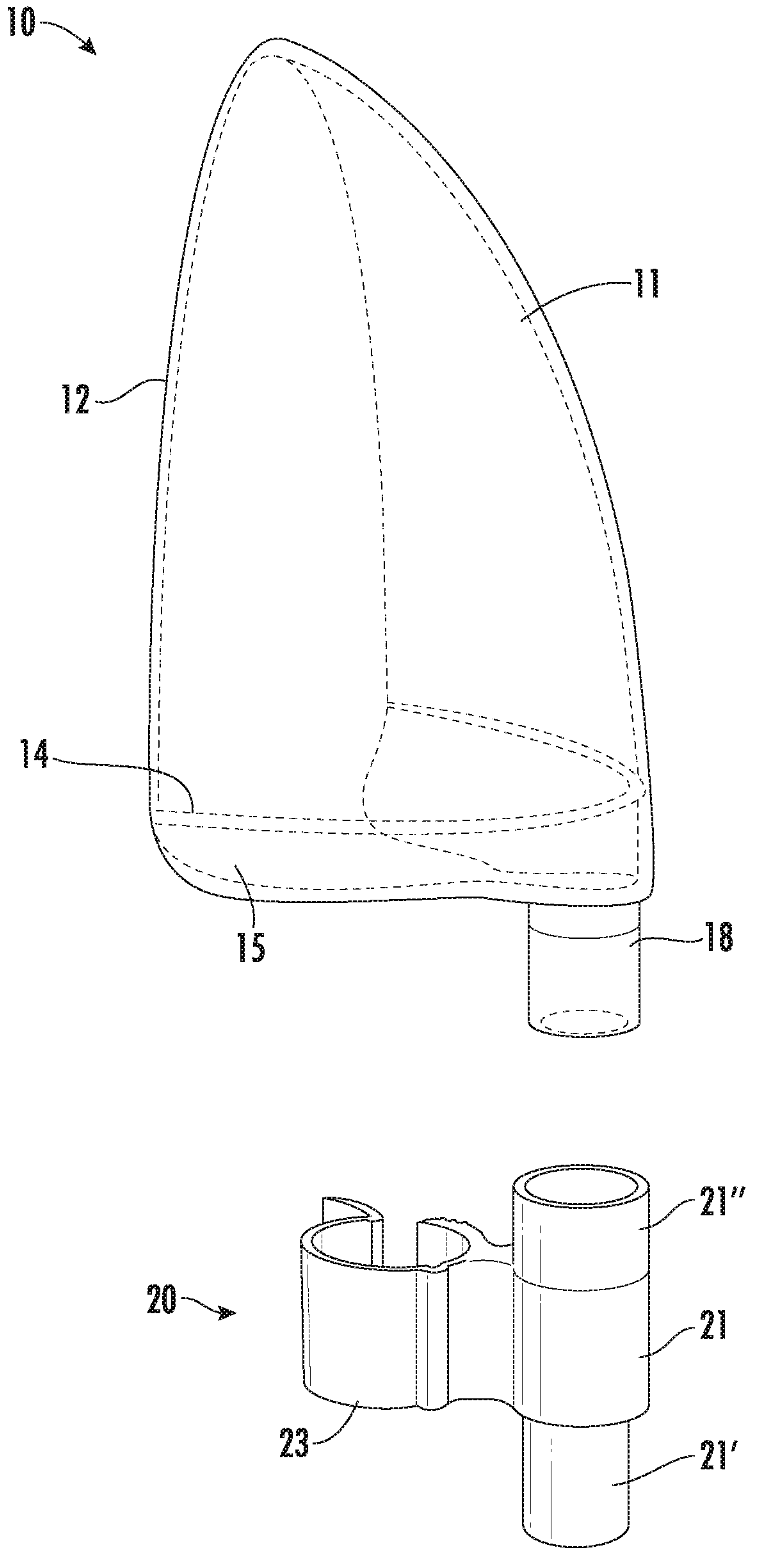
FIG. 9 is a perspective and partially exploded view of an even further embodiment of the vacuum shield assembly according to the present invention.
Figure 10:
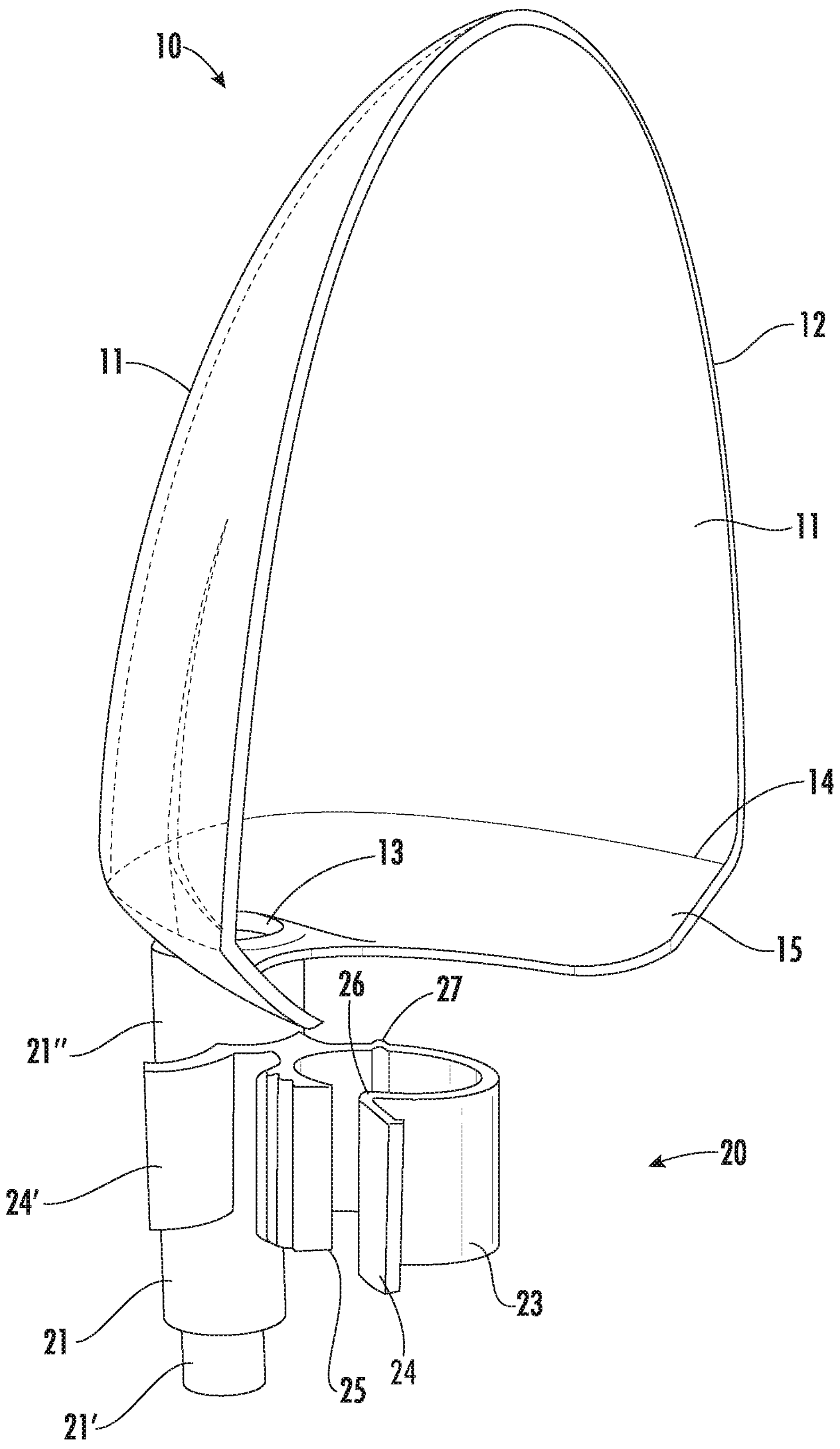
FIG. 10 is a perspective view of yet a further embodiment of the vacuum shield assembly according to the present invention.

With initial reference to FIGS. 1-4, 6-10 and 12, the present invention is directed to a vacuum shield assembly 10. The vacuum shield assembly 10 according to the present invention is intended to be disposed on the head and/or face of a patient that is already wearing a medical mask, and is intended to at least partially extract exhaled air from the patient. For example, and as is perhaps best shown in FIGS. 1 and 6, the vacuum shield assembly 10 may be attached to a mask already disposed on the head and/or face of a patient. The vacuum shield assembly 10 may be connected to a vacuum tube such that it may at least partially extract exhaled air from the patient, including, for example, between the already disposed medical mask and the inside of a shield body 11 of the vacuum shield assembly 10. The vacuum shield assembly 10 may serve as a primary suction or vacuum mechanism, or alternatively, as secondary suction or vacuum mechanism. As an example, and as is shown in FIGS. 6-8, the vacuum shield assembly 10 may be attached to a BIPAP or CPAP mask, or to a mask configured for oxygen delivery, which is already disposed on the head and/or face of a patient. Other possible existing medical masks that could be used in connection with the present invention include a face mask, a face tent, a Venturi mask, and/or a non-rebreather. As a further example, and as is shown in FIGS. 1-3, the vacuum shield assembly 10 may be attached to a nebulizing mask already disposed on the head and/or face of a patient.

As shown at least in the illustrative embodiments of FIGS. 1-4, 6-10 and 12, the vacuum shield assembly 10 comprises a shield body 11. The vacuum shield assembly 10 also generally comprises a retaining assembly 20. The retaining assembly 20 is generally connected to the shield body 11 as well as to a vacuum tube. As used herein, the term “vacuum tube” refers to a conduit, hose, or other related structure that may convey air from a patient and/or mask to another location, and which may be connected to a negative pressure vacuum. For example, the vacuum tube 40 may comprise a 22 millimeter hose, which may comprise a length of about 8 feet. As shown at least in FIGS. 2 and 7, the retaining assembly 20 may be used to interconnect the shield body 11 to a vacuum tube. The structure of the retaining assembly 20 should define a fluid communication between an inside of the shield body 11 and the vacuum tube. As such, the shield body 11 may create a negative pressure on an interior thereof to remove the air between the medical mask, the face and/or head of the patient, and the interior or inside of the shield body 11. It is contemplated that a patient that is wearing a BIPAP or CPAP mask, or a nebulizing mask, be able to exhale through the mask, and that at least a portion of this exhaled air may be captured by the negative pressure generated by the shield body 11 and the vacuum tube.

As is shown in FIGS. 1-2 and 6-7 the retaining assembly 20 may also be used to connect the shield body 11 and/or vacuum tube to an oxygen supply tube and/or a nebulizing unit or component thereof. Shield bodies of different sizes may be attached to a retaining assembly 20, for example, by inserting a connecting portion 18 into an upper section 21" of the retaining component 21, or to the retaining component 21 directly, which will be explained later. As such, it may be possible to switch between shield bodies of different sizes according to a specific need, e.g., air suction, nebulization, etc., and/or geometrical constraints, e.g., the size of the head of the patient.

Figure 12:
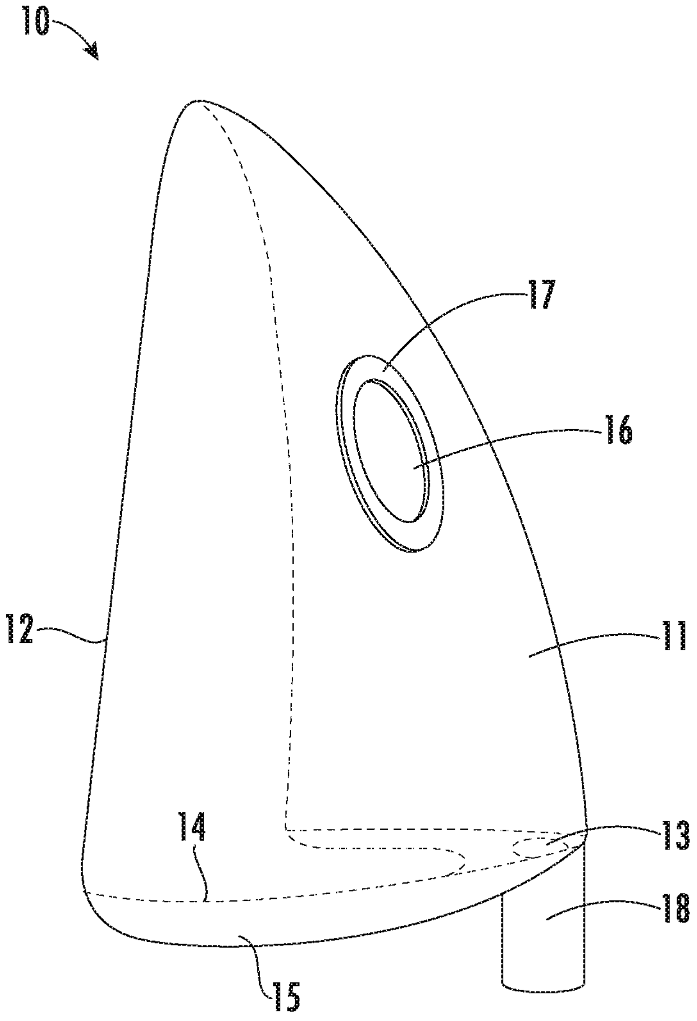
FIG. 12 is a perspective view of one embodiment of a shield body of the vacuum shield assembly according to the present invention comprising a second opening.
Figure 12A:
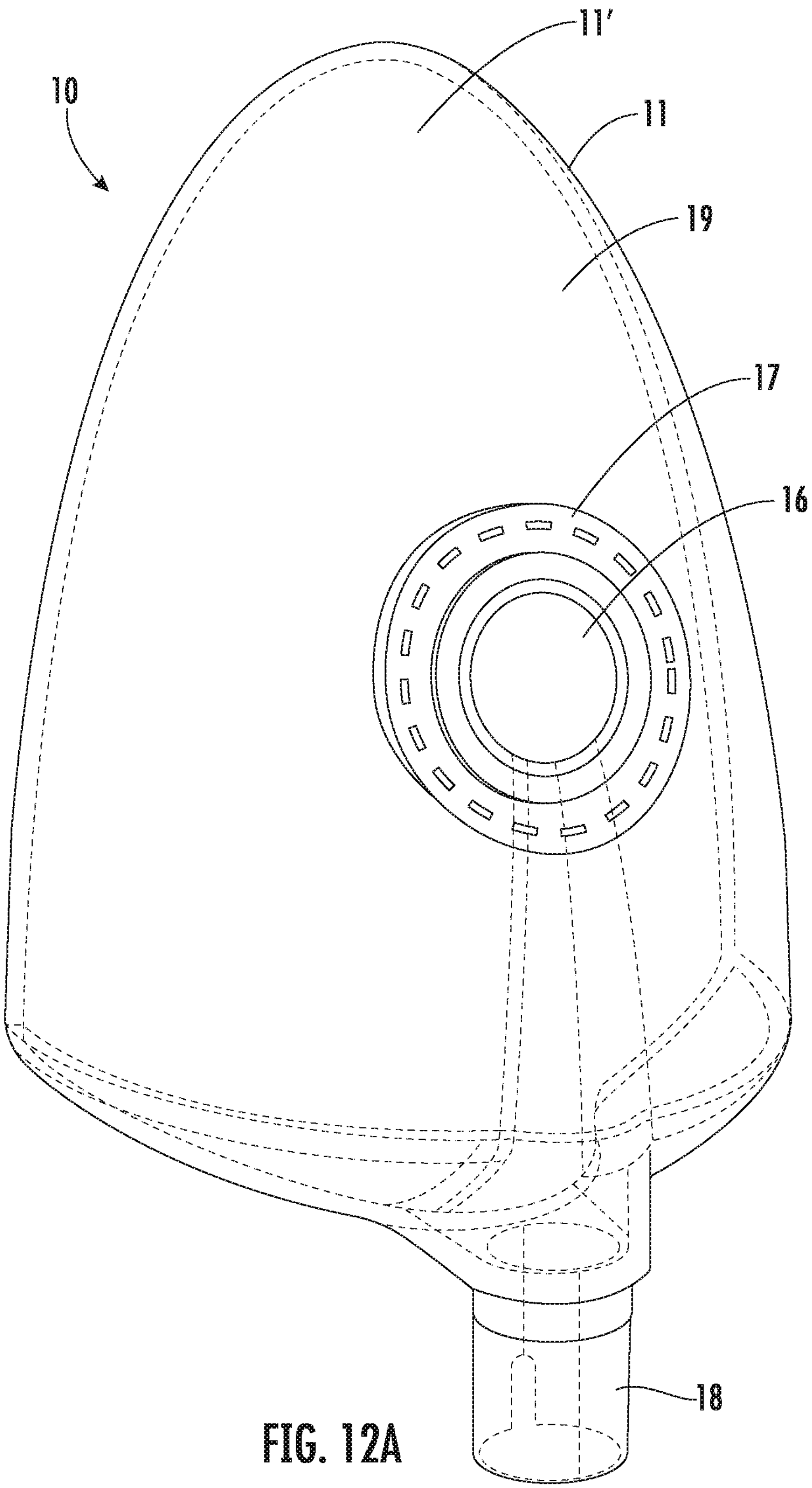
FIG. 12A is a perspective view of one embodiment of a shield body of the vacuum shield assembly according to the present invention comprising a second opening.
Figure 12B:
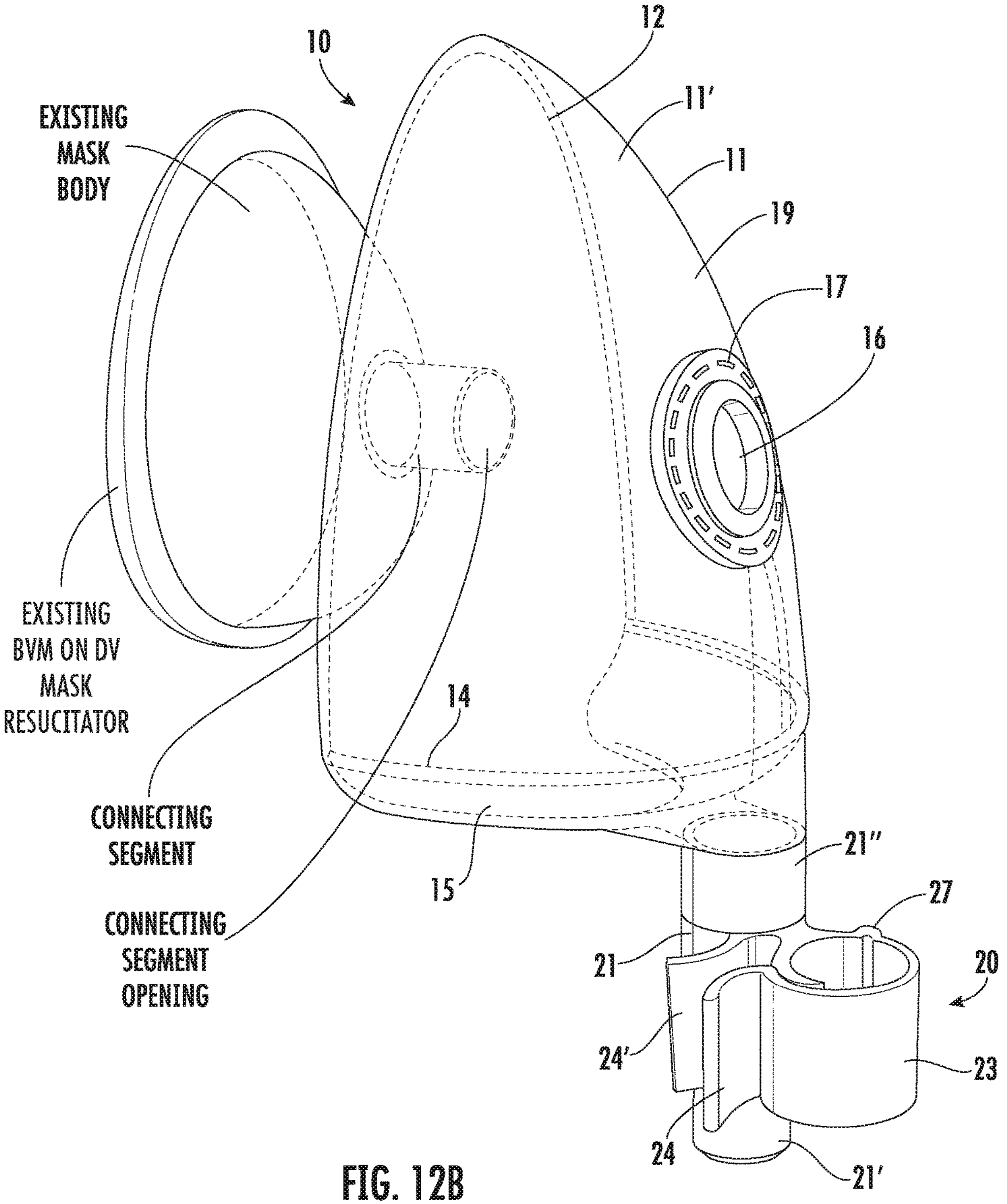
FIG. 12B is a perspective view of another embodiment of a shield body of the vacuum shield assembly according to the present invention comprising a second opening.
Figure 12C:
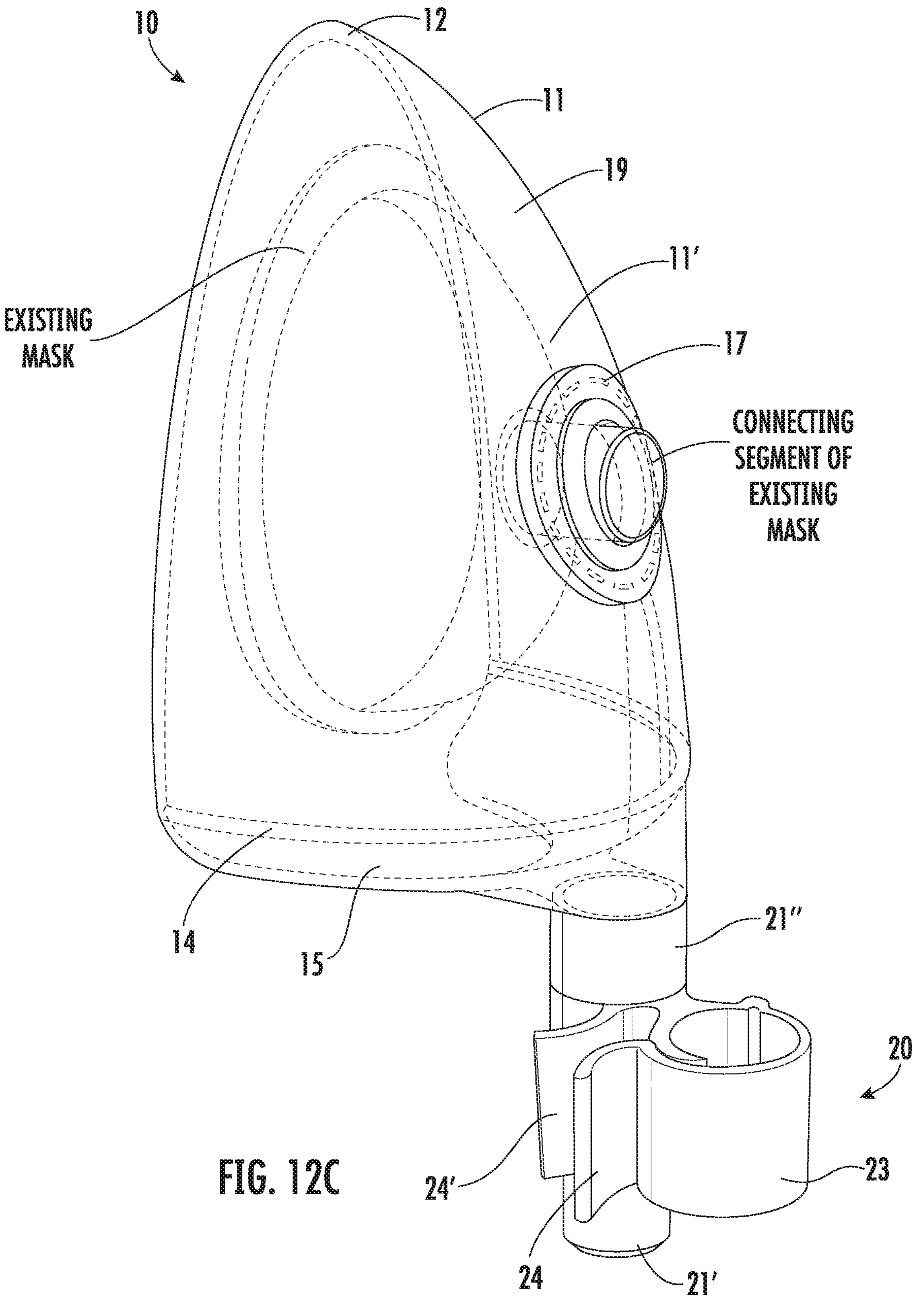
FIG. 12C is a perspective view of even another embodiment of a shield body of the vacuum shield assembly according to the present invention comprising a second opening.
Figure 12D:
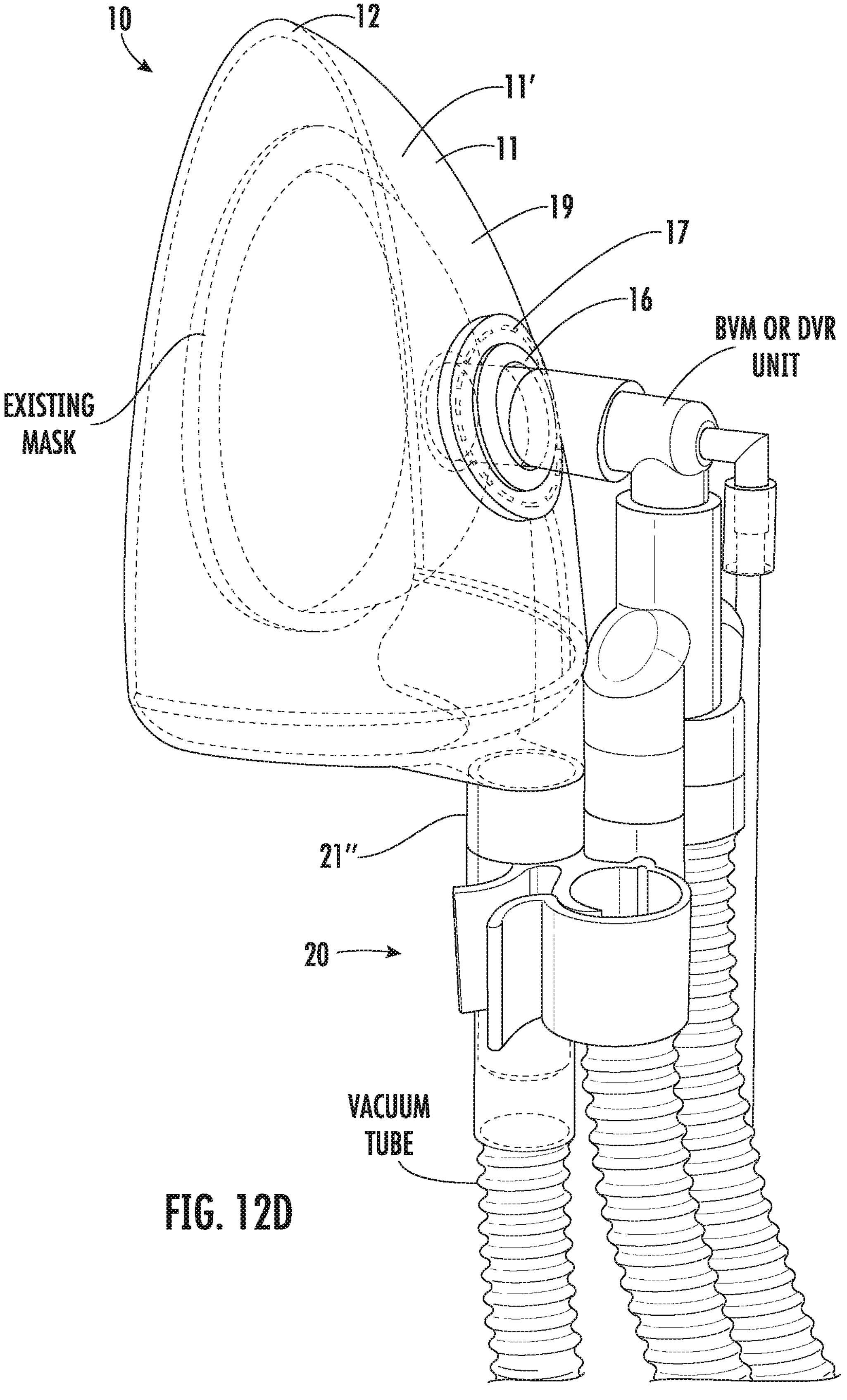
FIG. 12D is a perspective view of yet another embodiment of a shield body of the vacuum shield assembly according to the present invention comprising a second opening and connected to a BVM or DVR unit.
Figure 13A:
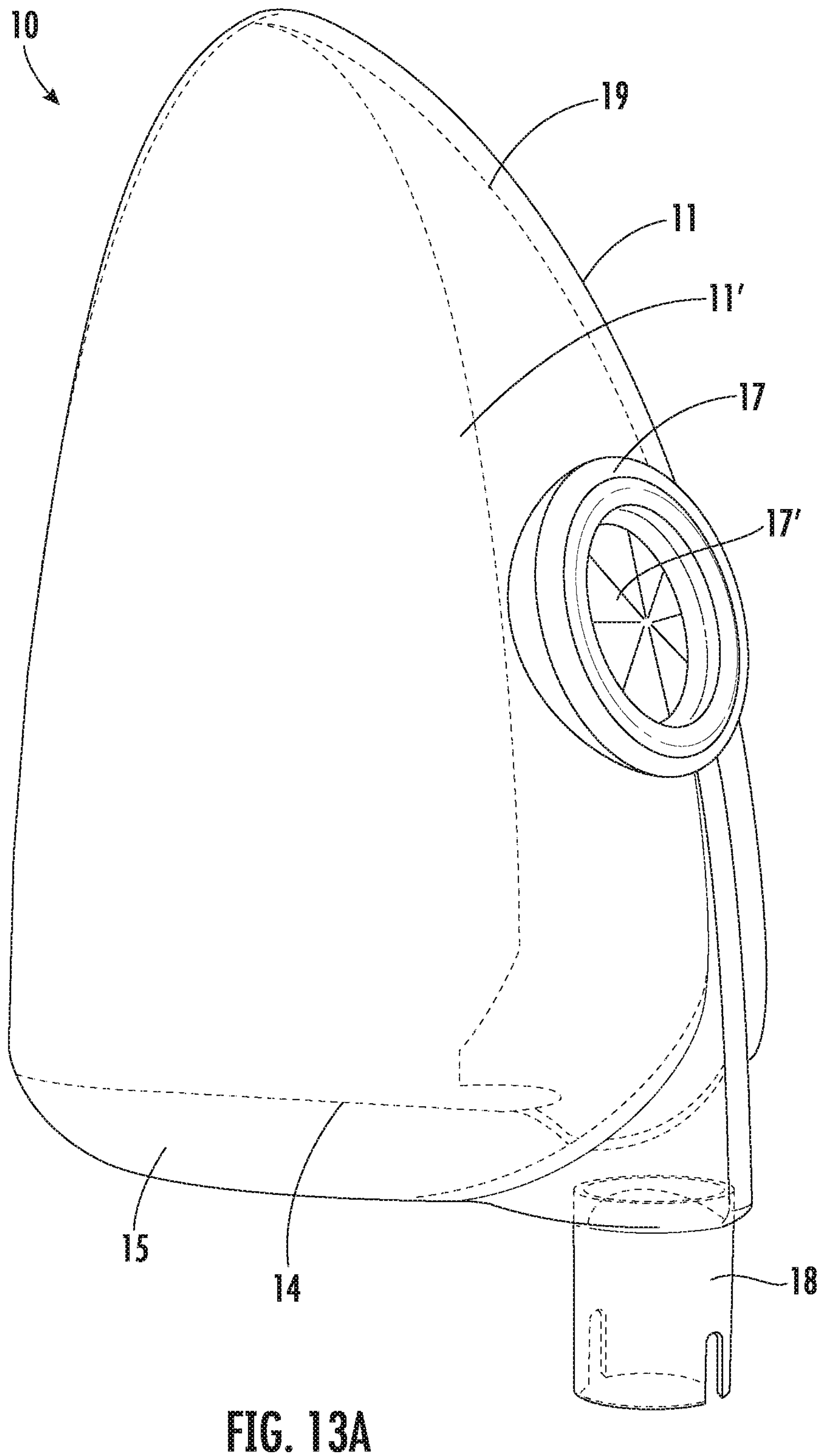
FIG. 13A is a perspective view of one embodiment of a shield body of the vacuum shield assembly according to the present invention comprising a vacuum attachment disposed on the shield body.
Figure 13B:
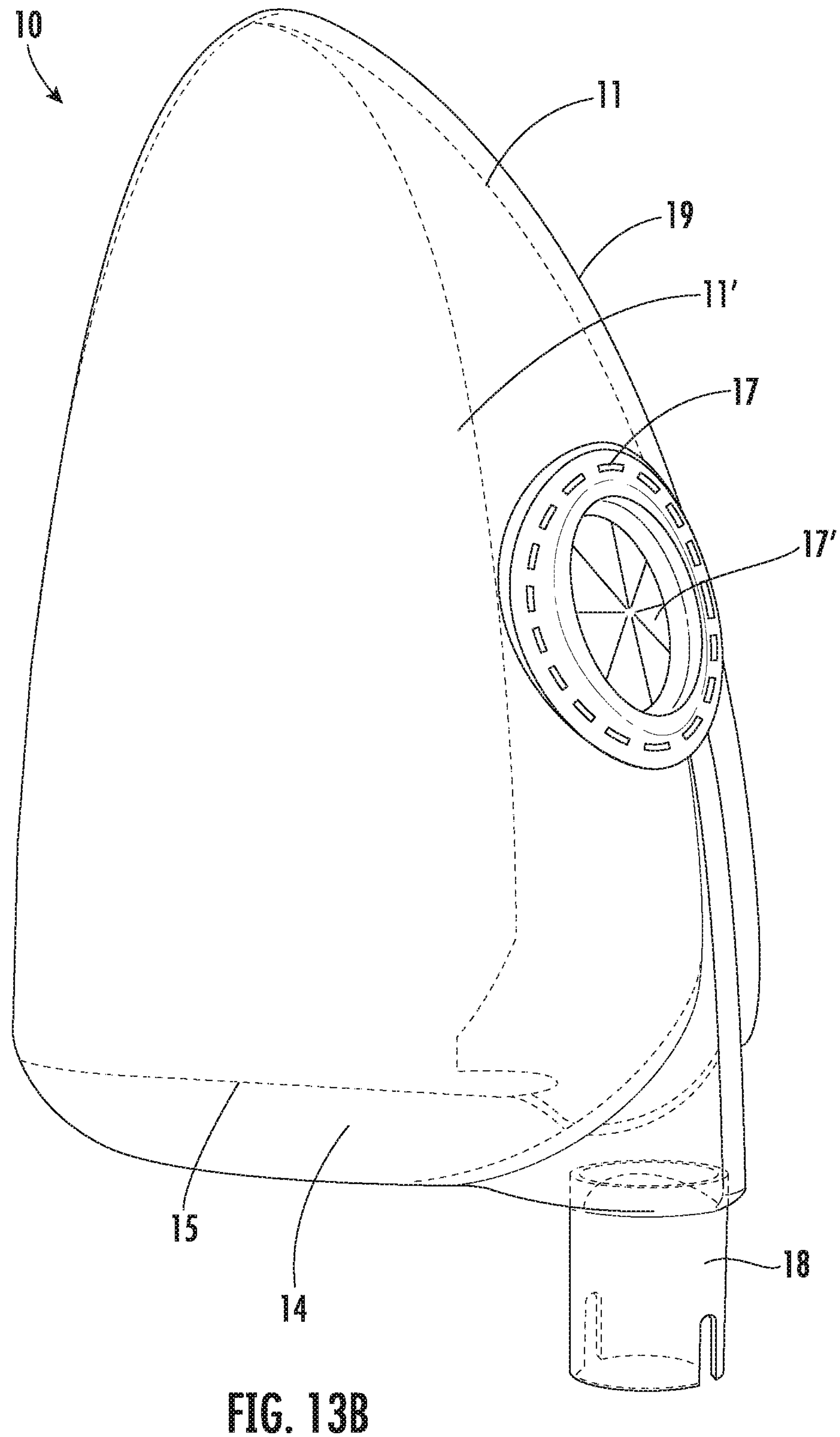
FIG. 13B is a perspective view of another embodiment of a shield body of the vacuum shield assembly according to the present invention comprising a vacuum attachment disposed on the shield body.
Figure 14A:
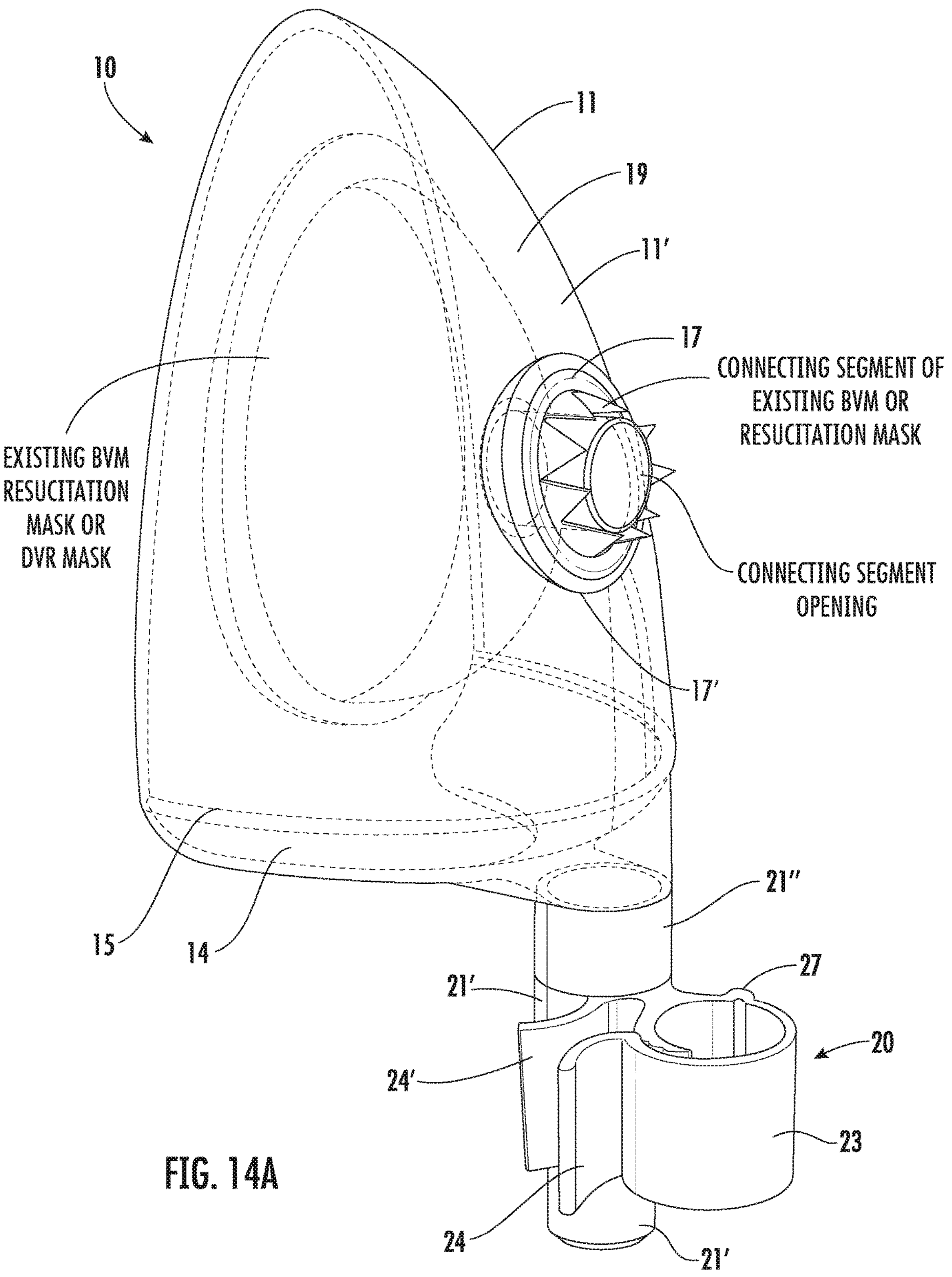
FIG. 14A is a perspective view of yet another embodiment of a shield body of the vacuum shield assembly according to the present invention comprising a vacuum attachment disposed on the shield body.
Figure 14B:
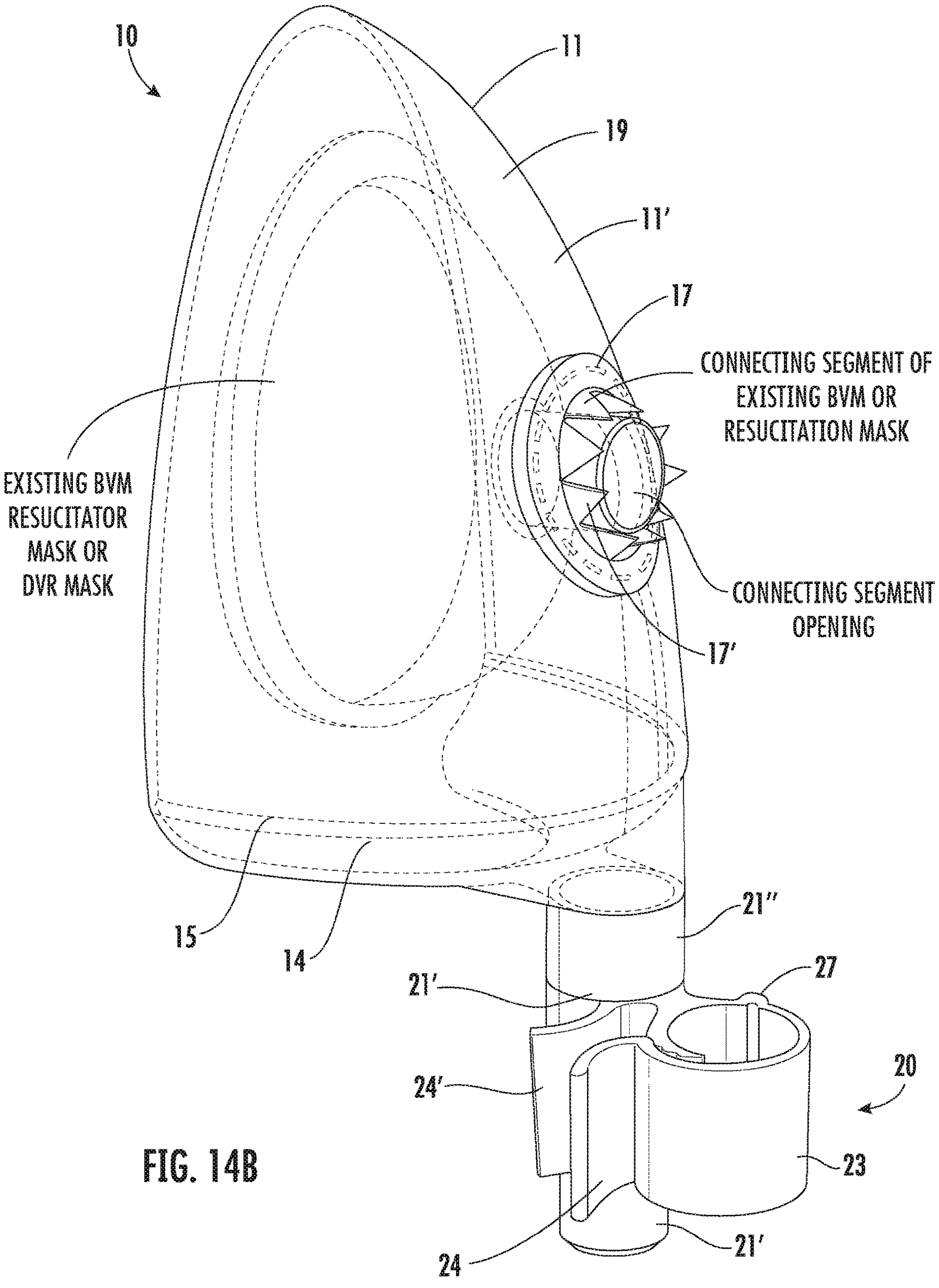
FIG. 14B is a perspective view of an even further embodiment of a shield body of the vacuum shield assembly according to the present invention comprising a vacuum attachment disposed on the shield body.
Figure 15A:
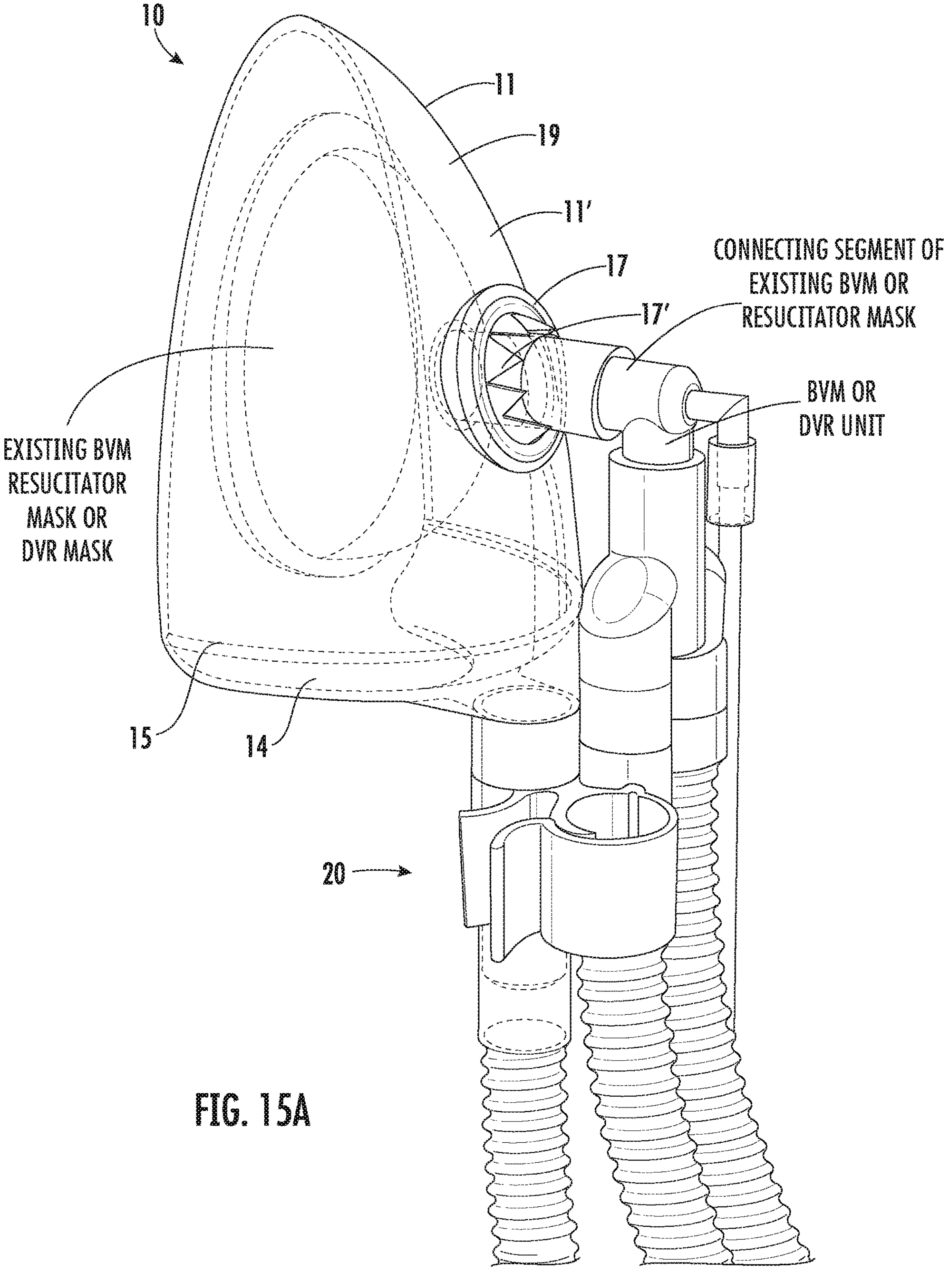
FIG. 15A is a perspective view of one embodiment of a shield body of the vacuum shield assembly according to the present invention comprising a vacuum attachment disposed on the shield body and connected to a BVM or DVR unit.
Figure 15B:
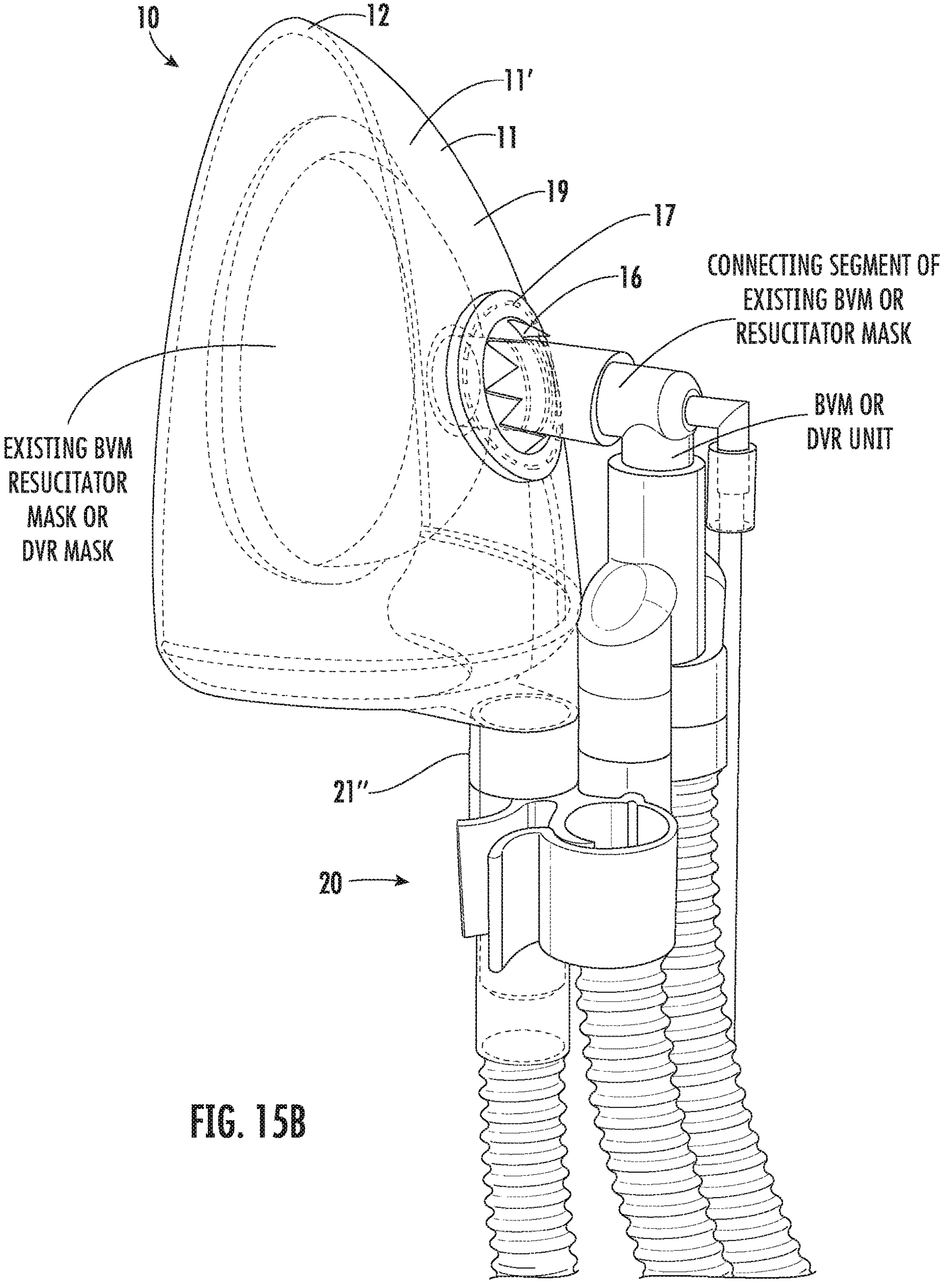
FIG. 15B is a perspective view of another embodiment of a shield body of the vacuum shield assembly according to the present invention comprising a vacuum attachment disposed on the shield body and connected to a BVM or DVR unit.

With reference to FIGS. 12A-15B, the shield body 11 according to the inventive vacuum shield assembly 10 may be provided with a second opening 16 configured and dimensioned to accommodate a medical mask. With specific reference to FIGS. 12B-12D and 14A-15B, the second opening 16 may be configured and dimensioned so that a connecting segment of an existing medical mask, e.g., a demand-valve resuscitator (DVR) mask or a bag-valve-mask (BVM) resuscitator mask, may be inserted there through, e.g., as shown in FIGS. 12D, 15A and 15B. Furthermore, the shield body 11 may be provided with a vacuum attachment 17, which may at least partially define or otherwise form a seal between an outer surface 11' and an inner surface 11" of the shield body 11. Also, the second opening 16 and/or vacuum attachment 17 may be operatively configured and dimensioned to substantially define a seal between the second opening 16 and the connecting segment of the medical mask. Accordingly, the vacuum attachment 17 may comprise a grommet component or grommet seal. However, this is not necessarily limiting as other configurations of the vacuum attachment 17 are also possible.

As represented in at least FIG. 15A, a grommet seal may be co-molded to the shield body 11. This is advantageous as it may at least partially reduce the time, effort, and/or expense involved in manufacturing a vacuum shield assembly 10 with a vacuum attachment. Further, a grommet seal co-molded to the shield body may provide for a robust construction, which is also advantageous. Alternatively, as represented at least in FIG. 15B, a grommet seal may be inserted into the shield body, which is referred to as an insert-molding. Further, the vacuum attachment 17 may comprise a variety of materials, including, but not necessarily limited to silicone, rubber, plastics, elastomeric polymers, seals, sealants, and/or other related structures. As such, the second opening 16 may at least partially allow an operative communication between the existing mask, i.e., BVM or DVR, through an interior of its connecting segment, and the underlying BVM or DVR unit. It is contemplated that the opening 16 permit at least a fluid communication between the existing mask and the BVM or DVR unit, i.e., via the interior of the connecting segment of the mask, which passes through the second opening 16.

With reference again to FIGS. 12A-15B, the second opening 16 may be disposed on the shield body 11 at a location that corresponds to the location of the medical mask. Generally, during some BVM and/or DVR procedures some air may leak between the face of the patient and the mask, which is attached to the patient, for example, as the patient inhales or exhales air. In such BMV and/or DVR procedures, the inventive vacuum shield assembly 10 is intended to capture exhaled air that may leak out of the BVM and/or DVR mask. As such, the second opening 16 may be disposed substantially around a middle section of the shield body 11 and/or above the first opening 13. This would allow for placement of the vacuum shield assembly 10 on a location that corresponds to location of the connecting segment of the medical mask. Moreover, the second opening 16 and/or vacuum attachment 17 may be disposed on a height along the shield body 11 that corresponds to the approximate location of the existing medical mask. As may be appreciated from the illustrative embodiments as shown in FIGS. 15A and 15B, exhaled air may exit through the existing mask, i.e. through opening 13 of the shield body 11. In addition to, or in lieu of this, exhaled air may also exit through a vacuum tube operatively connected to the existing mask and connecting segment, which passes through the second opening 16.

Figure 16A:
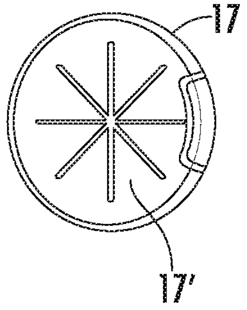
FIG. 16A is a top view of one embodiment of a vacuum attachment according to the vacuum shield assembly of the present invention.
Figure 16B:
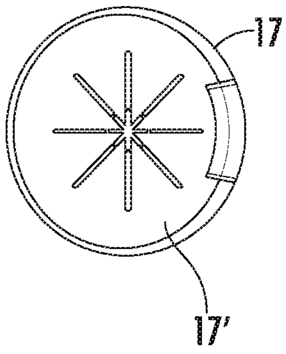
FIG. 16B is a top view of another embodiment of a vacuum attachment according to the vacuum shield assembly of the present invention.
Figure 16C:
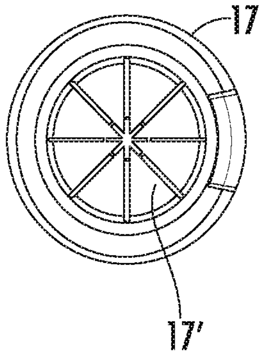
FIG. 16C is a top view of a further embodiment of a vacuum attachment according to the vacuum shield assembly of the present invention.
Figure 16D:
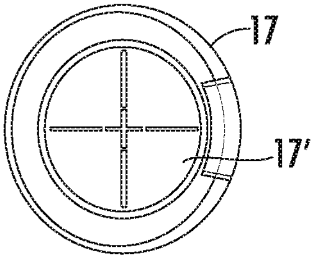
FIG. 16D is a top view of yet another embodiment of a vacuum attachment according to the vacuum shield assembly of the present invention.
Figure 16E:
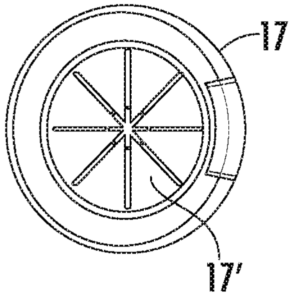
FIG. 16E is a top view of an even further embodiment of a vacuum attachment according to the vacuum shield assembly of the present invention.
Figure 16F:
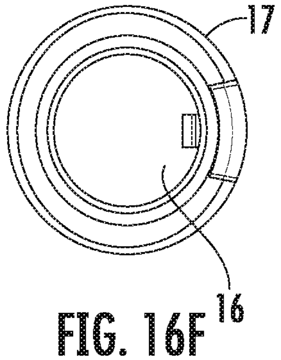
FIG. 16F is a top view of another embodiment of a vacuum attachment according to the vacuum shield assembly of the present invention.
Figure 16G:
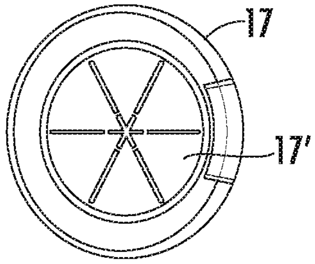
FIG. 16G is a top view of a further embodiment of a vacuum attachment according to the vacuum shield assembly of the present invention.
Figure 16H:
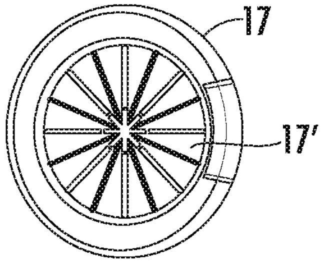
FIG. 16H is a top view of an even further embodiment of a vacuum attachment according to the vacuum shield assembly of the present invention.
Figure 16I:
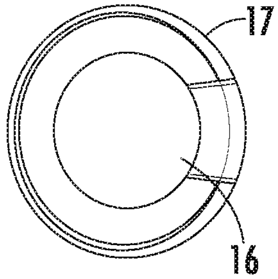
FIG. 16I is a top view of yet another embodiment of a vacuum attachment according to the vacuum shield assembly of the present invention.

As is perhaps best shown in FIGS. 16A-16I, features of the present invention comprise providing a vacuum attachment 17 comprising a grommet configuration. As shown in FIGS. 16A-16I, the vacuum attachment 17 may comprise a substantially circular shape configured to correspond to the diameter and/or size of the second opening 16. For example the diameter of an outer perimeter or recessed portion of the vacuum attachment 17 may be configured to correspond to the dimension and/or size of the second opening 16. Additionally, the circular shape of the vacuum attachment 17 may be configured and dimensioned to correspond to the diameter and/or size of the connecting segment of the medical mask, for example around an inner perimeter of the vacuum attachment 17. As shown in FIGS. 16F and 16I, a vacuum attachment 17 may be provided comprising a grommet configuration with an aperture. As such, when the vacuum attachment 17 is disposed around the second opening 16, the aperture of the vacuum attachment 17 permits a fluid communication between the outer surface 11' and inner surface 11" through the second opening 16. As shown in FIG. 16F, the vacuum attachment 17 may comprise a tear away recessed pocket. Conversely, as shown in the illustrative embodiments of FIGS. 16A-16E and 16G-16H, the vacuum attachment may comprise a grommet configuration that creates a cover around the interior perimeter of the vacuum attachment 17. The cover may comprise a plurality of adjacently disposed segments 17', which may be collectively structured to form a substantially flat surface in an inoperative disposition of the connecting segment of the medical mask, i.e., when the connecting segment is not inserted around the second opening 16. The plurality of adjacently disposed segments 17' may be collectively structured to bend at least in an opposite direction to the movement of the connecting segment of the medical mask.

As is shown in the illustrative embodiments of FIGS. 15A and 15B, once the connecting segment of the medical mask is inserted through the second opening 16, the plurality of adjacently disposed segments 17' may bend towards the outer surface 11' allowing the connecting segment to pass there through. Conversely, if the connecting segment is removed, the plurality of adjacently disposed segments 17' may return to their natural and/or initial positon, forming once again the cover around the aperture of the vacuum attachment 17. As such, a vacuum shield assembly 10 according to the present invention may be used in connection with one BVM and/or DVR procedure, then later removed, and used in a subsequent BVM and/or DVR procedure. The vacuum shield assembly 10 may also be used in connection with a procedure that uses the second opening 16, i.e., a BVM and/or DVR procedure, and may later be used in a subsequent procedure that does not use the second opening 16, or vice versa. Or alternatively, a vacuum shield assembly 10 comprising a second opening 16 may also be used in connection with a procedure that does not need the second opening 16. Thus, a vacuum shield assembly 10 comprising a second opening 16 may be attached to a medical mask that is not a BMV or DVR mask. As such, the plurality of adjacently disposed segments 17' may naturally form a cover, which should essentially function as a seal between the outer surface 11' and inner surface 11". Said differently, the plurality of adjacently disposed segments 17', in their natural position, should at least partially reduce leakage of exhaled air from the inner surface 11" to the outer surface 11'. As such, exhaled air may be retained on an interior of the shield body 11 and removed via the connecting portion 18 and/or oxygen tube.

As is also seen in FIGS. 16A-16E and 16G-16H, each one of the plurality of adjacently disposed segments 17' may comprise a substantially triangular shape. As such, when disposed around the inner perimeter of the vacuum attachment 17, they may substantially define a cover. By way of example, the plurality of adjacently disposed segments 17' comprising a substantially triangular shape may comprise four segments, e.g., FIG. 16D, six segments, e.g., FIG. 16G, eight segments, e.g., FIGS. 16A, 16B, 16C, 16E and 16H, or even more than eight segments. Furthermore, as shown in FIG. 16H, the plurality of adjacently disposed segments 17' may comprise reinforcement ribs. Also, the illustrative embodiments of FIGS. 16D-16E and 16G may comprise a top flush relief ring, or a recessed pocket as is shown in FIGS. 16C-16H. As shown in FIGS. 16A-16B, other possible configurations of the plurality of adjacently disposed segments comprises a top flush configuration without a relief ring.

As is perhaps best shown in FIGS. 5-6, and as mentioned below, the inventive vacuum shield assembly 10 comprises a retaining assembly 20. As shown in FIGS. 1 and 6, the retaining assembly 20 may be oriented towards the face of a patient, such that it may be used to attach the shield body 11 to an existing vacuum tube or other related component. Various connecting mechanism of the retaining assembly 20 may be implemented to connect it to the shield body 11, vacuum tube, oxygen supply tube or nebulizing unit. Said differently, the retaining assembly 20 may be used to interconnect the shield body 11 to the vacuum tube and the oxygen supply tube, an existing nebulizing unit and/or mask, or an existing BIPAP or CPAP mask. As an example, the retaining assembly 20 may comprise clamps or connecting arms. Other mechanisms of the retaining assembly 20 are also within the scope of the present invention and may comprise adhesives, connecting bands, snap-on mechanisms, magnets, or another related connecting mechanisms.

Figure 5:
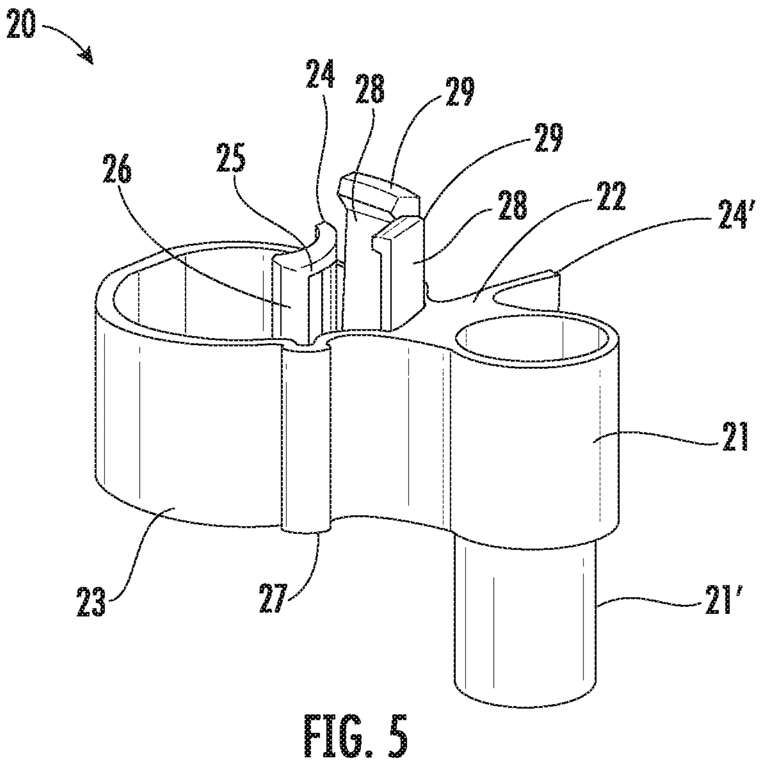
FIG. 5 is a perspective view of one embodiment of a retaining assembly of the vacuum shield assembly according to the present invention.
Figure 11:
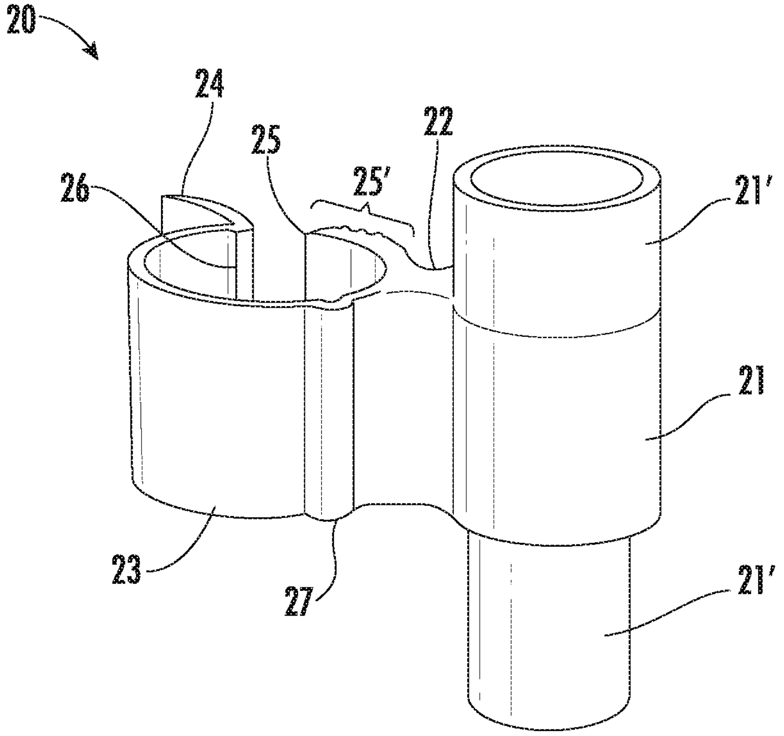
FIG. 11 is a perspective view of another embodiment of a retaining assembly of the vacuum shield assembly according to the present invention.

As seen in the illustrative embodiments of FIGS. 5 and 11, the retaining assembly 20 may comprise a retaining frame 23 connected to a retaining component 21. As mentioned above, a connecting portion 18 of the vacuum shield assembly 10 may be configured and dimensioned to correspond to the size of a retaining component 21 of the retaining assembly 20. As may be appreciated from FIG. 11, sometimes it may be beneficial to provide for a height adjustment for the point of connection between the connecting portion 18 of the shield body 11 and the retaining assembly 20. In such embodiments, the retaining component 21 may be provided with an upper section 21", which may at least partially raise the position of the shield body 11 relative to the point of attachment of the retaining assembly 20 to the oxygen supply tube or other related component of the existing mask.

Additional features of the present invention comprise providing a shield body 11 that may be configured and dimensioned to correspond to the geometry and/or size of the head and/or face of patient and/or the existing mask and its components. It is within the scope of the present invention that when the shield body 11 is disposed against the existing mask that a substantial portion of the edge 12 at least partially surround the existing mask. That is, the shield body 11, including the edge 12 of the perimeter, should define a profile or area that is at least equal to or even greater than the profile or area of the existing mask. As such, exhaled air from the patient will be retained on an inside of the shield body 11, including above a lower segment 15. As an example, as is shown at least in FIGS. 4 and 9-10, the edge 12 may comprise a semi-ovoidal configuration. As is perhaps best shown in FIGS. 4 and 9, the edge 12 may also define a substantially flat side profile of the shield body 11. However, the shield body 11 may comprise other shapes to correspond to the shape of the existing mask. The lower segment 15 may be configured and dimensioned to accommodate the size and/or geometry of an oxygen supply tube of a BIPAP or CPAP mask, or the size and/or geometry of a nebulizer unit and/or components thereof.

The illustrative embodiment of FIGS. 6-9 and 11 show a retaining assembly 20 comprising a retaining component 21 and an upper section 21" thereof which provides for a vertical offset. The length of the upper section 21" may be configured and dimension according to preferences, type of existing mask, intended application, amount of height adjustment needed for the shield body 11, etc. These illustrative embodiments, both of the retaining component 21 and the upper section 21" comprise a substantially cylindrical configuration with approximately the same diameter. Conversely, as is in the illustrative embodiments of FIGS. 1-5, the retaining assembly 20 may be provided with a retaining component 21 without an upper section 21". It is within the scope of the present invention that the connecting portion 18 of the shield body 11 be attachable to the retaining component 21 and/or upper section 21" thereof. For example, the connecting component 18 may comprise a substantially cylindrical configuration, which may be configured and dimensioned to correspond to the size of an inside of a cylindrical retaining component 21 and/or upper section 21". Further to this example, and as is perhaps best shown in FIGS. 4 and 9, the outer diameter of the connecting component 18 may be at least partially smaller than the inner diameter of the retaining component 21 and/or upper section 21", such that the connecting component 18 may be inserted into the retaining component 21 and/or upper section 21". In at least one embodiment the retaining component 21 and upper section 21" may comprise the same diameter. Additionally, in such embodiments, both diameters of the connecting component 18, retaining component 21 and/or upper section 21" may be configured and dimensioned to enable a frictional resistance between corresponding surfaces such that the shield body 11 may be connected to the retaining assembly 20, and further, so that it may remain in place during periods of operation or use of the inventive vacuum shield assembly 10.

As may be perhaps best shown in the illustrative embodiments of FIGS. 2-5 and 7-11, the retaining component 21 of the retaining assembly 20 comprises a lower section 21'. The inside of the lower section 21' of the retaining component 21 should be disposed in fluid communication with the inside of the retaining component 21, the inside of the connecting portion 18 of the shield body 11, the inside of the upper section 21" of the retaining component, and/or the inside of the vacuum tube. Additionally, the lower section 21' of the retaining component 21 may be configured and dimensioned for attachment of the vacuum tube. By way of example only, the lower section 21' of the retaining component 21 may be provided with an outer diameter that is at least partially smaller to an inner diameter of the vacuum tube. As such, the vacuum tube may be attached to the outside of the lower section 21' of the retaining component 21, and may be disposed in fluid communication with an inside of the lower section 21' of the retaining component 21, the inside of the retaining component 21, an inside of the upper section 21" of the retaining component 21, and/or an inside of the connecting portion 18. This should enable a fluid communication between the vacuum tube and the shield body 11, including on an interior or inside thereof, which is perhaps best shown in FIG. 10. As such, activation of the vacuum tube will result in a negative pressure around the inside of the shield body 11. Such a negative pressure will result in at least a partial removal of the air on the inside of the shield body 11 and/or the surrounding area.

With reference to at least FIGS. 5 and 11, and as mentioned above, the retaining assembly 20 may be provided with a retaining frame 23. The retaining frame 23 may be connected to the retaining component 21, for example, via a transition structure 22. The retaining frame 23 is intended to attach the retaining assembly 20, and consequently the shield body 11 and vacuum tube, to a component of the existing mask. For example, such a component of the existing mask may include an oxygen supply tube of a BIPAP of CPAP mask. Also as an example, such a component of the existing mask may also include a nebulizing unit or a portion or component thereof. The retaining frame 23 should comprise an inner area, which may be selectively adjusted to securely retain the oxygen supply tube or nebulizing unit or component thereof. For example, the retaining frame 23 may comprise a substantially cylindrical configuration and/or two segments which may be connected to one another. A first closing structure 25 and a second closing structure 26 may be provided and may be cooperatively configured to form a closing mechanism or engagement that retains the oxygen supply tube or nebulizing unit. Also as an example, the first closing structure 25 and/or second closing structures 26 may be provided with a closing mechanism or related components that may enable such closing mechanism or engagement.

In the illustrative embodiments of FIGS. 1-11, a first closing structure 25 may be provided with a snap component whereas a second closing structure 26 may be provided with serrations 25'. The snap component and the serrations 25' may be cooperatively configured with one another to form a mating engagement, and allow a user or medical practitioner to selectively increase or decrease the inner area of the retaining frame 23. For example, the snap may be selectively disposed in any one of a plurality of serrations 25' along the length of one of the segments of the retaining frame 23. As used herein, a "snap" mechanism generally refers to a single-snap mechanism, or a multi-snap mechanism, i.e., an adjustable mechanism that may be selectively disposed into various size settings. As such, one single retaining assembly 20 may be used in connection with various oxygen supply tubs of different sizes and/or nebulizer units of different sizes. To further assist the user or medical practitioner in adjusting the inner area or opening of the retaining frame 23, one or more flaps 24 and/or 24' may be provided. The flaps 24 and/or 24' may be disposed or otherwise formed on the segments of the retaining frame 23, including around the first closing structure 25 and/or second closing structure 25. The flaps 24 and/or 24' may extend along the height of the retaining frame 23 and/or may comprise a size that corresponds to the size of the thumbs and/or fingers of a user or medical practitioner. Thus, selective movement of the flaps 24 and/or 24 will result in a corresponding movement of at least one of the segments of the retaining frame 23, and consequently movement of a corresponding closing structure 25 and/or 26. Although a retaining assembly 20 may be provided comprising two flaps 24 and 24', it is also possible to provide a retaining assembly 20 comprising only one flap 24 or one without any flaps.

As is perhaps best show in in FIG. 5, the retaining frame 23 may be provided with at least one retaining segment 28 configured to at least partially retain the nebulizing unit. For example, as shown in the illustrative embodiment of FIG. 3, two retaining segments 28 may be used to at least partially retain a middle section of a nebulizing unit. Further, each retaining segment(s) 28 may comprise latch 29 disposed around an upper end thereof. The latch(es) 29 may be configured to hold the top of the middle section of the nebulizing unit in place and at least partially reduce its movement in the vertical direction. As is also shown in the illustrative embodiment of FIG. 3, and also in other embodiments, the retaining frame 23 may be provided with a substantially cylindrical or semi-cylindrical configuration. Such configuration is advantageous to retain or otherwise attach the retaining assembly 20 to substantially cylindrical nebulizers or oxygen supply tubes.

With reference now to at least FIGS. 1-3 and 6-8, features of the present invention comprise providing a vacuum shield assembly 10 with a shield body 11 and a retaining assembly 20 collectively disposable into and out of an operative position and an inoperative position. As used herein, the "inoperative position" refers to a position of non-use of the vacuum shield assembly 10, and may include a storage position, an inactive position, a position where the vacuum shield assembly is not connected to external components, e.g., an oxygen supply tube, vacuum tube, nebulizer unit, face or head of a patient, etc. Conversely, as used herein, the "operative position" refers to an operational or otherwise active positon of the vacuum shield assembly 10. In the operative position, the shield body 11 should be connected to and disposed in fluid communication with the retaining assembly 20. As is shown at least in FIGS. 1-3 and 6-8, in the operative position, an interior or inside of the shield body 11 should be oriented toward the existing mask, which should already be disposed on the face and/or head of the patient. In the operative position, the vacuum tube, and/or connected vacuum source, should exert a negative pressure, which should result on a corresponding exerted negative pressure around the shield body 11 and the surrounding area. It is contemplated that in the operative position, the negative pressure exerted around the inside or interior of the shield body 11, and/or above the lower segment 15, should be sufficient to at least partially extract the exhaled air form the patient. Also, the lower segment 15, along with the interior or inside of the shield body 11, is intended to at least partially retain exhaled air between the face of the patient and/or existing mask, and the shield body 11. As such, movement of the exhaled patient air outside of the area surrounding the shield body 11 may be at least partially reduced, such that, the negative pressure of the vacuum tube, should result on an efficient removal of the exhaled air.

With reference to FIGS. 17-19D, further embodiments of the present invention relate to a system 1' configured to remove exhaled air from a patient. Generally, the system 1' according to the present invention is configured to remove exhaled air from a patient wearing a medical mask as defined herein, but may also be used on patients not wearing a medical mask as the various components of the system 1' may be at least partially disposed on the patient directly. With specific reference to at least FIGS. 17 and 18, the system 1' generally comprises at least a vacuum shield assembly 10 as defined herein, a retaining assembly 20 as defined herein, a vacuum tube 40 and a vacuum unit 80. In embodiments of the present invention where the shield body 11 may be disposed directly on a patient not wearing a medical mask, a retaining assembly 20 may not be necessary as the vacuum tube 40 may be disposed directly on the shield body 11. As used herein, a vacuum unit 80 refers to a vacuum device, which may be motor operated, and which may be disposed in fluid communication with a vacuum tube 40, i.e., a hose, or other flexible or expandable hollow elongated component, and which may exert a negative pressure. It is contemplated that a shield body 11 of the shield assembly 10 also be disposed in fluid communication with the interior of the vacuum tube 40. The negative pressure of the vacuum unit 80 should be transferred through the vacuum tube 40, and to an interior face of the shield body 11, i.e., the side that faces the patient. As such, the shield body 11 essentially acts as a vacuuming device that is capable of at least partially removing exhaled air around the face of the patient. As used herein, the space defined by the interior face of the shield body 11 as well as the face of the patient, including when wearing the medical mask, is defined as an enclosure zone 19.

Figure 18A:
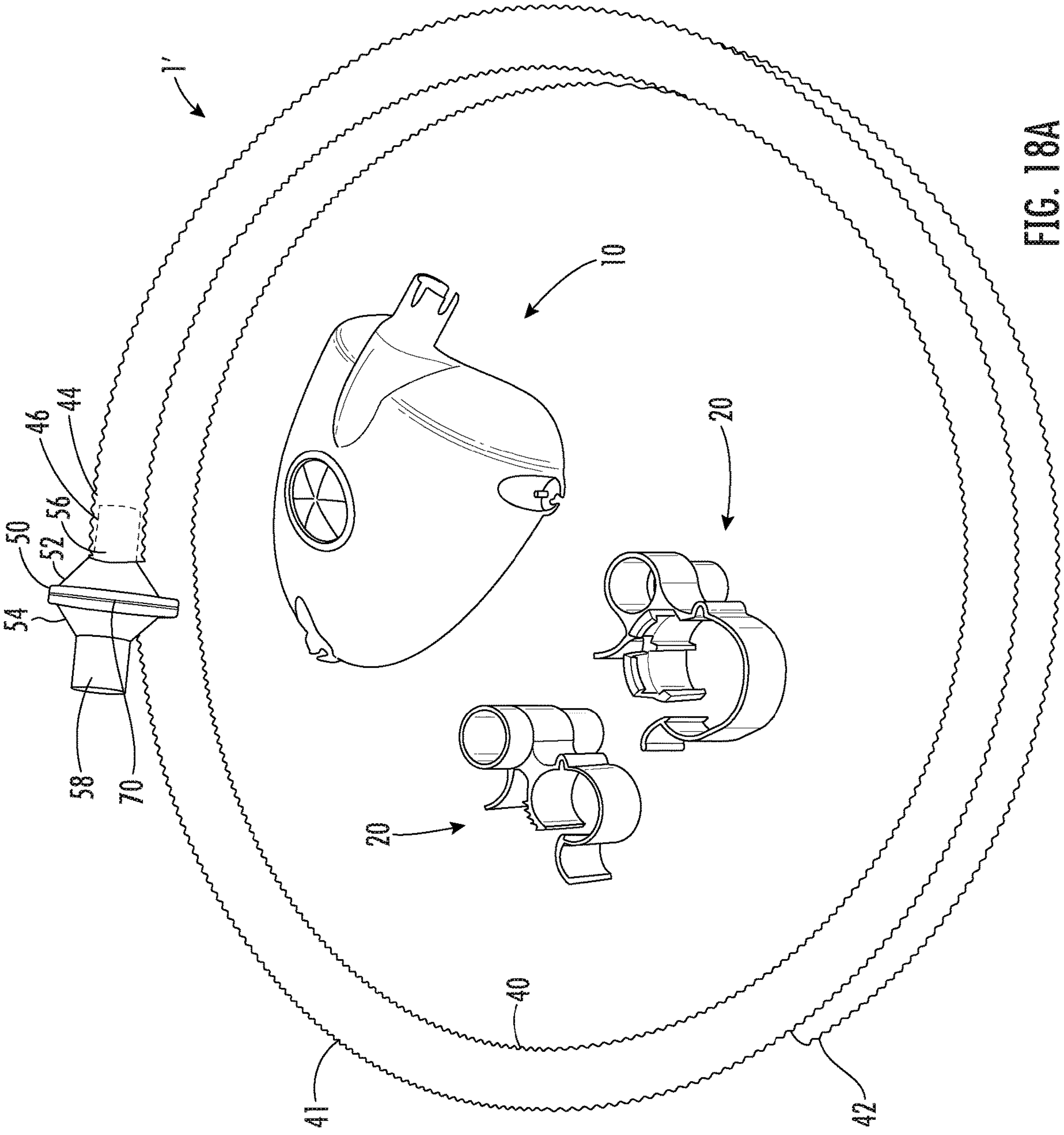
FIG. 18A is a perspective view of disassembled components of one embodiment of the system according to the present invention.

With reference to at least FIG. 18A, the system 1' according to the present invention may comprise a retaining assembly 20 configured to retain the vacuum tube 40 and a component of the medical mask as defined herein, i.e., an oxygen supply tube of a BIPAP of CPAP mask or a nebulizing unit or a portion or component thereof. Further, the vacuum tube 40 may comprise a body 41 of a flexible, or elastic material that may at least partially bend, twist, move or otherwise conform to geometric constraints. The vacuum tube 40 may comprise a proximal end 44 that connects to the vacuum unit 80 around connecting end 36, and a distal end 42 that connects to the shield body 11 around a connecting end 46.

Figure 18B:
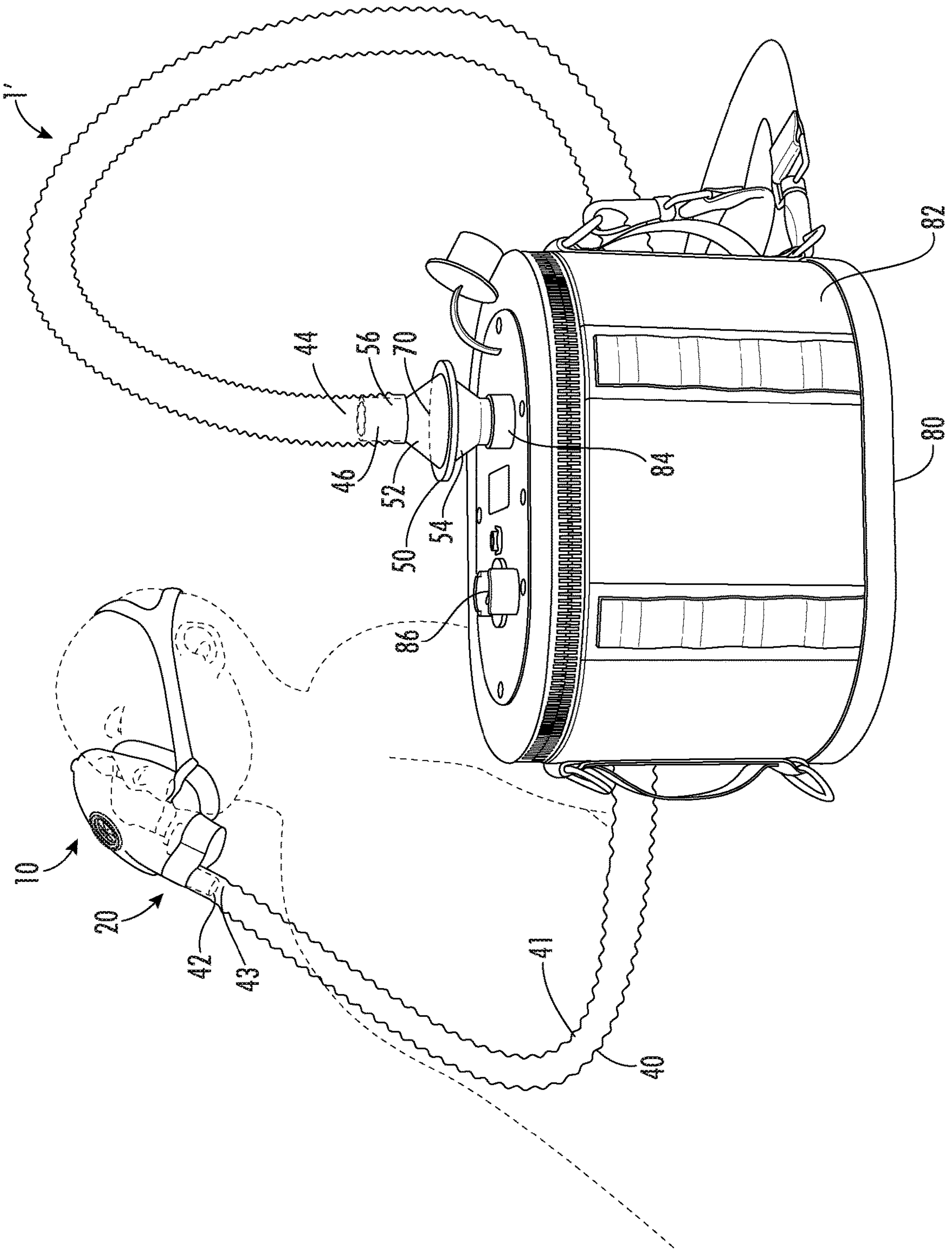
FIG. 18B is a perspective view of another embodiment of the system according to the present invention.

With reference to at least FIGS. 18A-18B, a filter case assembly 50 may be disposed or integrally formed on the vacuum tube 40 around the proximal end 44. The filter case assembly 50 may comprise a top segment 52 and a bottom segment 54 which may be operatively connected to one another. In other words, the top segment 52 and bottom segment 54 may form a mating engagement with one another in a secured position, i.e., once a filter 70 has been placed between them. It is contemplated that the mating engagement between top segment 52 and bottom segment 54 not be a permanent mating engagement such that the top segment 52 and bottom segment 54 may be removably connected to one another to insert and/or remove a filter in the area where they engage. The diameters of the top segment 52 and/or bottom segment 54 should correspond to one another and should be configured and dimensioned to accommodate the diameter and/or size of a filter 70, which may comprise an air filter such as an ultra-low particulate air (ULPA) filter. The filter 70 may also comprise a high efficiency particulate air (HEPA) filter. As such, the diameters of the top segment 52 and/or bottom segment 54 may be larger than the diameter of the vacuum tube 40, but this is not strictly necessary. When the top segment 52 and the bottom segment 54 are forming a mating engaged, this should restrict placement or otherwise movement of a filter 70 disposed therein. Furthermore, the top segment 52 and/or upper segment 54 may be provided with conical or semi-conical shapes. This may be done to at least partially facilitate airflow through the vacuum tube 40 and into the vacuum unit 80 and/or to otherwise at least partially reduce the likelihood of a bottleneck effect around the area where the filter 70 is disposed. Consequently, air captured around a distal end 42 of the vacuum tube will pass through the filter 70 before entering the vacuum unit 80, at least partially reducing contaminants and/or other infectious particles.

Figure 17:
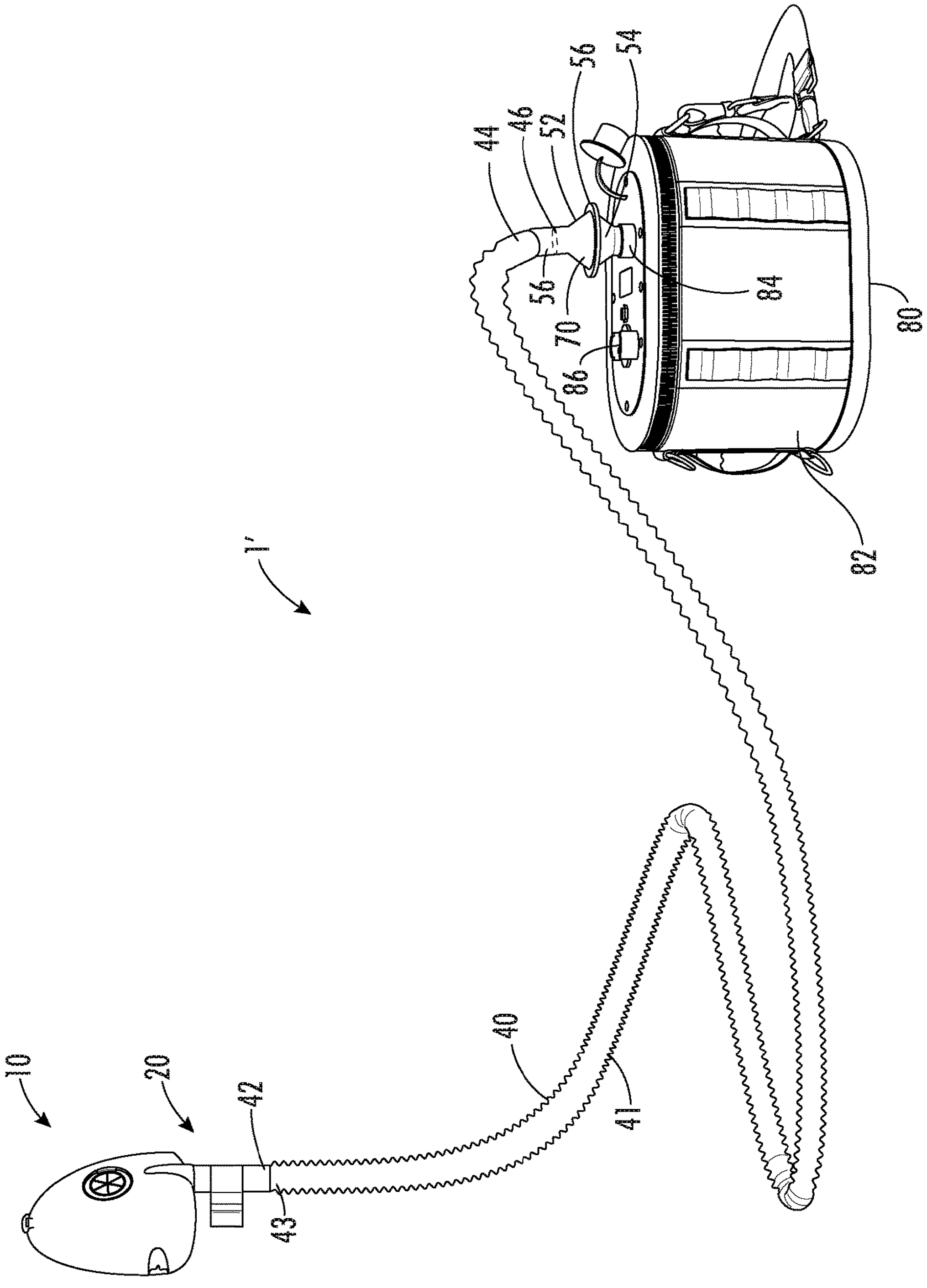
FIG. 17 is a perspective view of one embodiment of the system according to the present invention.

With reference to at least FIGS. 17 and 18B, and as mentioned above, the system 1' according to the present invention comprises a vacuum unit 80. The vacuum unit 80 should provide for a portable solution of creating a negative vacuum pressure, at least around its first opening 84 where the vacuum tube 40 will be connected. The vacuum unit 80 may comprise a housing 82 with a first opening 84 and a second opening 86. The first opening 84 is generally configured for attachment of the vacuum tube 40, for example, around a proximal end 44 thereof. The second opening 86 is generally configured for captured air to exit outside of the housing 82. That is, air collected form the enclosure zone 19 that passes through the first opening 84 and into the interior of the housing 82, should be able to exit outside of the housing 82 through the second opening 86. Alternatively, other means of air escape may be provided on the housing, and may include slots or vents, including disposed on the sides. In addition, the interior of the housing 82, which is generally a chamber, may be provided with other filtering means to further remove contaminants and/or infections particles form the air captured around the enclosure zone 19. Also, a top cover of the housing may be removable from the rest of the housing 82 to access any components thereof, which may include a battery-operated vacuum with a motor, additional filtering components, etc. By way of example only, a battery-operated vacuum motor of 110V or similar, may be provided on an inside of the housing 82.

Specific to the system 1' according to the present invention, the vacuum unit 80, vacuum tube 40 and shield body 11 may be collectively disposable into and out of an operative orientation and an inoperative orientation. The operative orientation comprises the vacuum unit 80 activated and exerting a negative pressure on an inside of the shield body 11, i.e., around the enclosure zone 19, to at least partially remove exhaled patient air. The inoperative operation comprises periods of non-operation of the system 1', including when the vacuum unit 80 is inactive. Also, the shield body 11, the vacuum tube 40 and the retaining assembly 20 may be collectively disposed into and out of an operative position and an inoperative position. With reference to FIG. 18B, the operative position generally comprises the shield body 11 at least partially attached to the head of the patient and the vacuum tube 40 operatively connected to the shield body 11. The operative position may also comprise the vacuum tube 40 and the component of the medical mask disposed onto the retaining assembly 20. The operative orientation may also comprise disposing the shield body 11, the vacuum tube 40 and the retaining assembly 20 into the operative position and the vacuum unit 80 being activated to exert a negative pressure on the inside of the vacuum tube 40 as well as the interior of the shield body 11, at least partially removing exhaled air from the patient around the enclosure zone 19. In at least one embodiment of the system 1' according to the present invention, the system 1' is capable of removing at least 93% of exhaled particles having a size of 0.5 micron. In order to achieve this, the system 1' should be capable of delivering a negative pressure of at least 240 liters per minute, measured around the interior of the shield body 11, and in some embodiments up to about 280 liters per minute. In turn, this at least partially achieves a re-breathing or re-inhalation reduction of up to about 6%, while at the same, given the geometry of the components of the shield body 11, does not substantially reduce the amount of inhaled oxygen, i.e., from an oxygen supply tube, or nebulizer particles. In some embodiments the amount of nebulizer particles provided to the patient is maintained, and in other embodiments, even increased.

Figure 19D:
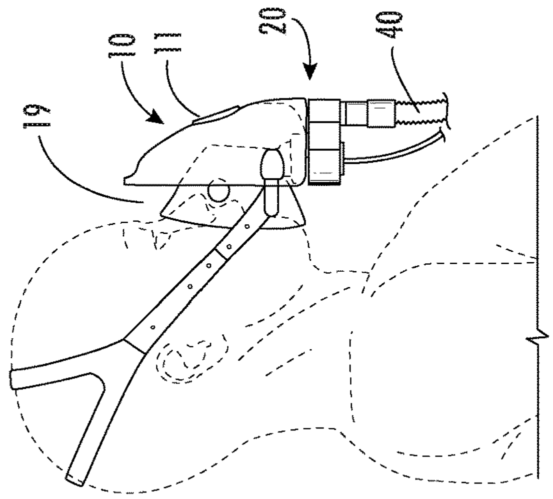
FIG. 19D is a perspective side view of a further embodiment of the shield and retaining assembly of the system according to the present invention disposed on an existing medical mask attached to a patient.
Figure 19C:
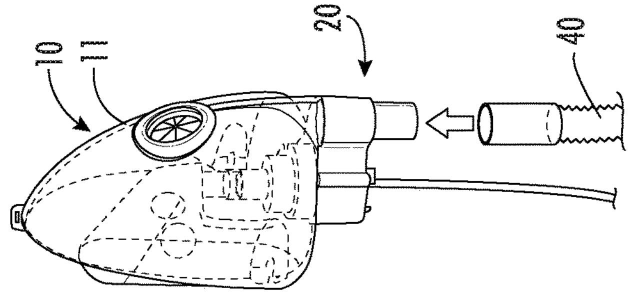
FIG. 19C is a perspective side view of yet another embodiment of the shield and retaining assembly of the system according to the present invention attached to a nebulizer.
Figure 19B:
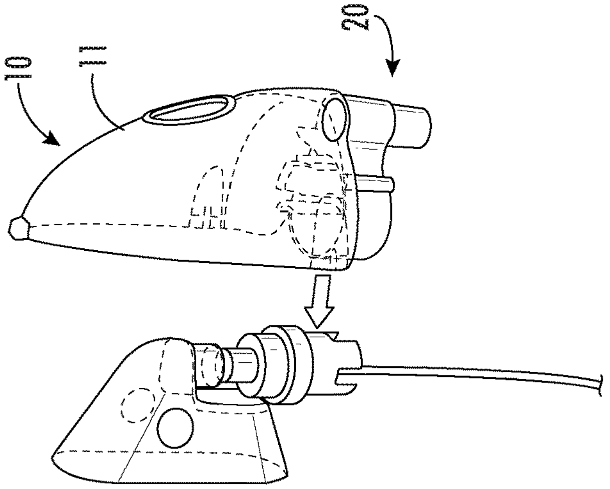
FIG. 19B is a perspective side view of another embodiment of the shield and retaining assembly of the system according to the present invention before attachment to a nebulizer.
Figure 19A:
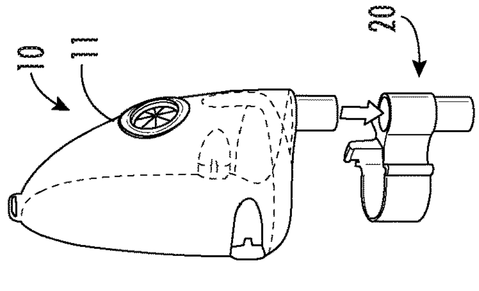
FIG. 19A is a perspective side view of one embodiment of the shield body and retaining assembly of the system according to the present invention.
Figure 20D:
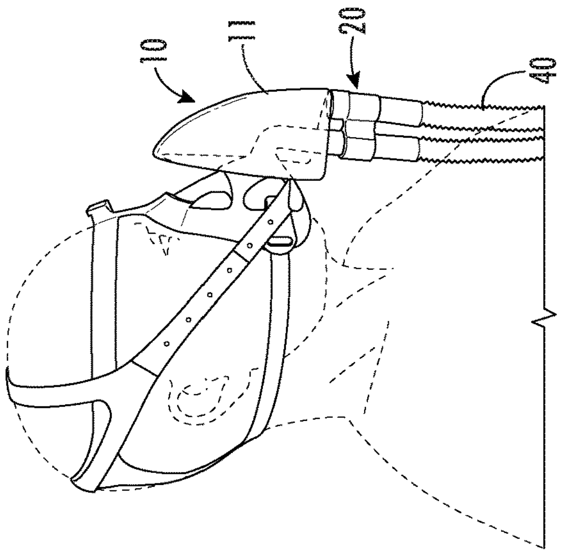
FIG. 20D is a perspective side view of a further embodiment of the shield and retaining assembly of the system according to the present invention disposed on an existing medical mask attached to a patient.
Figure 20C:
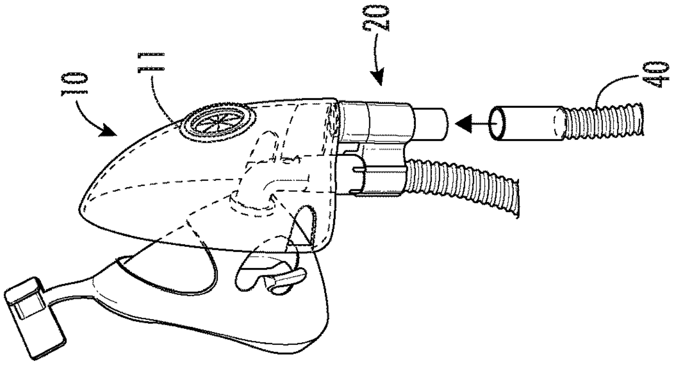
FIG. 20C is a perspective side view of yet another embodiment of the shield and retaining assembly of the system according to the present invention attached to an oxygen supply tube.
Figure 20B:
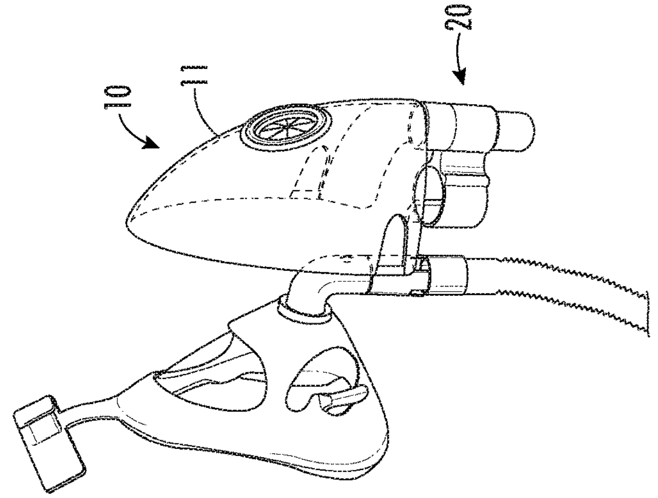
FIG. 20B is a perspective side view of another embodiment of the shield and retaining assembly of the system according to the present invention before attachment to an oxygen supply tube.
Figure 20A:
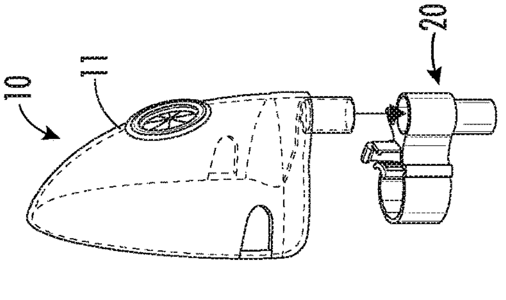
FIG. 20A is a perspective side view of one embodiment of the shield body and retaining assembly of the system according to the present invention.
Figure 21A:
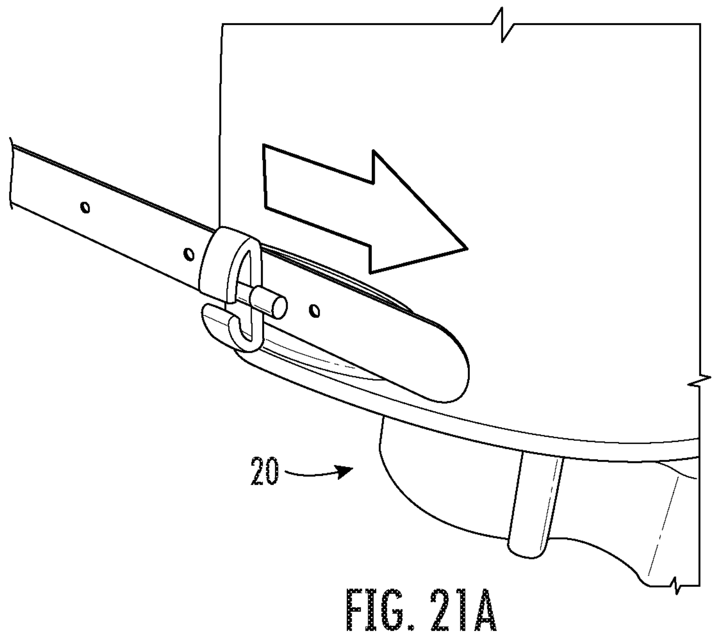
FIG. 21A is a perspective view of a portion of one embodiment of the system according to the present invention comprising a strap for an existing mask and a retaining assembly attached to a nebulizer.
Figure 21C:
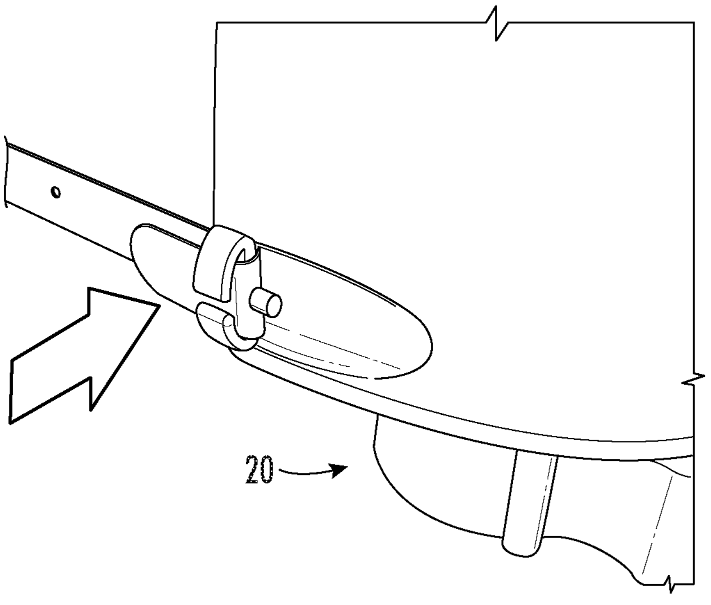
FIG. 21C is a perspective view of a portion of yet another embodiment of the system according to the present invention comprising a strap for an existing mask and a retaining assembly attached to a nebulizer.
Figure 21B:
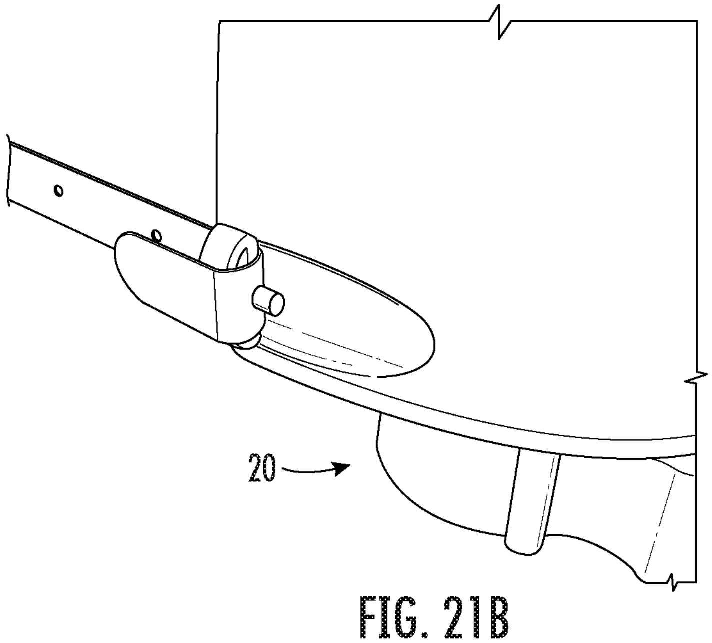
FIG. 21B is a perspective view of a portion of another embodiment of the system according to the present invention comprising a strap for an existing mask and a retaining assembly attached to a nebulizer.
Figure 21D:
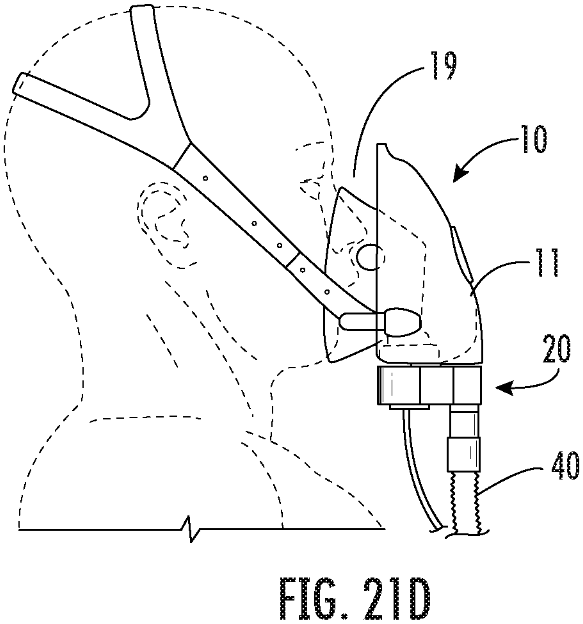
FIG. 21D is a perspective view of one embodiment of the system according to the present invention comprising a body shield attached to a medical mask and a patient.

With reference now to at least FIGS. 19A-21D, and as mentioned above, various components of the innovative system 1' may be disposed into an operative position as shown in FIGS. 19D, 20D and 21D. The shield body 11 may be connected to the retaining assembly (FIGS. 19A and 20A). Thereafter, the retaining assembly 20 may be connected to an oxygen supply tube of an existing mask (FIG. 20B), or to a nebulizer (FIG. 19B). Thereafter, the vacuum tube 40 may be connected to the retaining assembly 20 (FIGS. 19C and 20C). In some embodiments where a medical mask or existing mask is provided with an adjustable strap. The strap may be inserted between the outer surface of the mask and a retaining component (FIG. 21A) and one of a plurality of adjustable holes of the strap may be inserted into a retaining element to adjust the length of the strap (FIG. 21B). The remaining portion of the strap may be secured the side structures of the retaining component (FIG. 21C).

Figure 22:
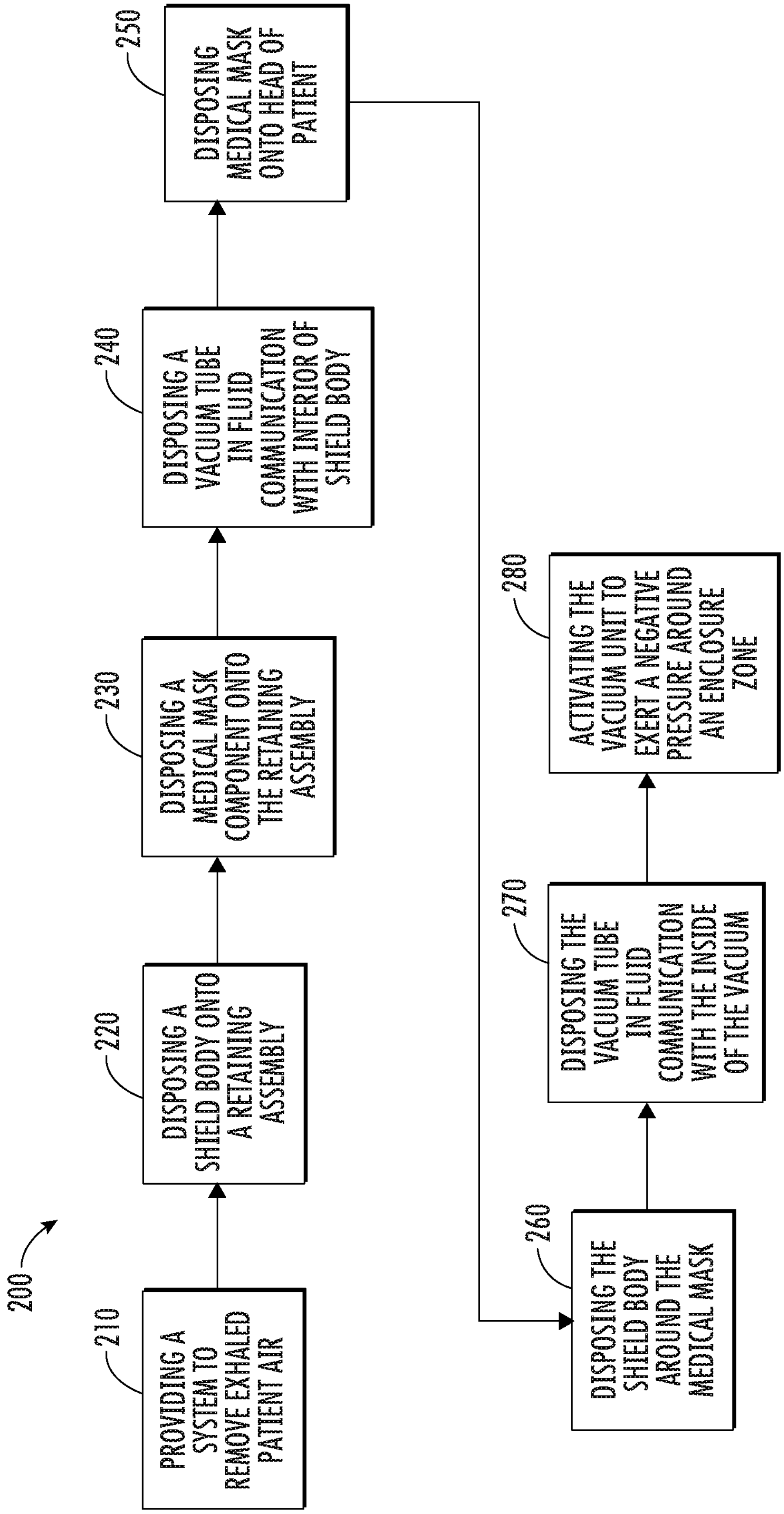
FIG. 22 is a diagrammatic representation of one embodiment of the method according to the present invention for removing exhaled air from a patient.

With reference now to at least FIG. 22, the present invention is also directed towards a method 200 of removing exhaled air from a patient. As shown at 210, the method 200 comprises providing (i) providing a system 1' as defined herein configured to remove exhaled air from the patient wearing the medical mask. The system 1' may comprise: a vacuum unit 80, a vacuum tube 40; an air filter 70 operatively disposed on an inside of the vacuum tube 40; a vacuum shield assembly 10 comprising a shield body 11 that is disposable onto the patient wearing the medical mask; and a retaining assembly 20 structured to retain the vacuum tube and a component of the medical mask; wherein the vacuum tube 40 is disposed in fluid communication with an inside of the shield body 11 and the vacuum unit 80, and wherein the vacuum tube 40, the shield body 11 and the vacuum unit 80 are collectively disposable into and out of an operative orientation and an inoperative orientation. The method 200 may further comprise: (ii) disposing the shield body 11 onto the retaining assembly 20, which is shown at 220; (iii) disposing the component of the medical mask onto the retaining assembly 200, which is shown at 230; (iv) disposing the vacuum tube 40 in fluid communication with an inside of the shield body 11, which is shown at 240; (v) at least partially disposing the medical mask on the head of the patient, which is shown at 250, and (vi) at least partially disposing the shield body 11 around the medical mask, which is shown at 260. The method 200 may further comprise at least partially disposing the shield body 11 around the medical mask comprises at least partially disposing the shield body 11 around the medical mask and in proximity to the face of the patient creating an enclosure zone 19. As shown at 270, the method 200 may further comprise (vii) disposing the vacuum tube in fluid communication with an inside of the vacuum unit, and as shown at 280 (viii) activating the vacuum unit to exert a negative pressure on the enclosure zone and remove exhaled air from the patient. The method 200 may further comprise (viii) activating the vacuum unit 80 to exert a negative pressure on the inside of the vacuum tube 40 and on the inside of the shield body 11 to remove exhaled air from the patient between the inside of the shield body 11 and the face of the patient.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A system configured to remove exhaled air from a patient wearing a medical mask, the system comprising:
   - a vacuum tube,
   - a vacuum shield assembly disposable onto the patient wearing the medical mask, the vacuum shield assembly comprising a shield body,
   - said shield body comprising a connecting portion disposed in fluid communication with said vacuum tube, a retaining assembly structured to retain said vacuum tube and a component of the medical mask, said retaining assembly comprising:

a retaining component configured and dimensioned to retain said connecting portion of said shield body, a lower section of said retaining component configured and dimensioned for attachment of said vacuum tube, and a retaining frame connected to said retaining component and configured to retain the component of the medical mask, a vacuum unit, said vacuum unit disposed in fluid communication with said vacuum tube and an inside of said shield body, and said vacuum unit, said vacuum tube and said shield body collectively disposable into and out of an operative orientation and an inoperative orientation, wherein:

said shield body comprises a concave configuration, said retaining assembly of said vacuum shield assembly is structured to retain a vacuum tube and at least one of an oxygen supply tube, a bag-valve-mask resuscitator unit, a demand-valve resuscitator unit, or a nebulizer unit of the medical mask, said shield assembly further comprises a lower segment comprising an opening and disposed around a lower perimeter of said shield body, said lower segment is configured for attachment to the vacuum tube and configured to exert a negative pressure on an inside of said shield body, and said shield body, said vacuum tube and said retaining assembly collectively disposable into and out of an operative position and an inoperative position.

2. The system recited in claim 1 wherein said operative orientation comprises:

said vacuum unit configured to be activated and exerting a negative pressure on an inside of said shield body at least partially removing exhaled air from the patient.

3. The vacuum shield assembly as recited in claim 1 wherein said operative orientation comprises:

said shield body configured to be at least partially attached to the head of the patient, said vacuum tube operatively connected to said shield body, and said vacuum tube and the component of the medical mask disposed onto the retaining assembly.

4. The vacuum shield assembly as recited in claim 1 wherein said concave configuration of said shield body is dimensioned and configured to at least partially surround the medical mask.

5. The vacuum shield assembly as recited in claim 1 wherein said lower segment comprises a substantially curved configuration; said shield body further comprises an edge defining a substantially flat side profile of said shield body; and said edge comprises a semi-ovoidal configuration.

6. The vacuum shield assembly as recited in claim 1 wherein the connecting portion is disposed in fluid communication with said opening of said shield body and configured for attachment to said vacuum tube.

7. The vacuum shield assembly as recited in claim 1 wherein said retaining frame comprises a semi-cylindrical configuration.

8. The vacuum shield assembly as recited in claim 1 wherein said retaining assembly comprises a first closing mechanism comprising a plurality of serrations; said retaining assembly further comprising a second closing mechanism comprising a snap mechanism operatively configured and dimensioned with said plurality of serrations to adjust the size of said retaining frame.

9. A system configured to remove exhaled air from a patient wearing a medical mask, the system comprising:

a vacuum tube, a retaining assembly structured to retain said vacuum tube and an oxygen supply tube or a nebulizer unit of the medical mask, a vacuum shield assembly disposable onto the patient wearing the medical mask, the vacuum shield assembly comprising:

a shield body comprising a concave configuration, a lower segment comprising an opening and disposed around a lower perimeter of said shield body, said lower segment configured for attachment to the vacuum tube and configured to exert a negative pressure on an inside of said shield body, said shield body further comprising a connecting portion disposed in fluid communication with said vacuum tube, said retaining assembly comprising:

a retaining component configured and dimensioned to retain said connecting portion of said shield body, a lower section of said retaining component configured and dimensioned for attachment of said vacuum tube, and a retaining frame connected to said retaining component and configured to retain the oxygen supply tube or the nebulizer unit of the medical mask, said shield body, said vacuum tube and said retaining assembly collectively disposable into and out of an operative position and an inoperative position, a vacuum unit, said vacuum tube disposed in fluid communication with an inside of said vacuum unit and an inside of said shield body around its opening, and said vacuum unit, said vacuum tube and said vacuum shield collectively disposable into and out of an operative orientation and an inoperative orientation.

10. The system as recited in claim 9 wherein said operative position comprises:

said shield body configured to be at least partially attached to the head of the patient, said vacuum tube operatively connected to said shield body, and said vacuum tube and the component of the medical mask disposed onto the retaining assembly.

11. The system recited in claim 9 wherein said operative orientation comprises:

said vacuum unit configured to be activated and exerting a negative pressure on said inside of said vacuum tube and on said inside of said shield body at least partially removing exhaled air from the patient wearing the medical mask.

12. The system as recited in claim 10 wherein said vacuum unit comprises a housing and a battery-operated motor vacuum disposed on an inside of said housing.

13. The system as recited in claim 10 wherein said vacuum unit comprises a housing with at least one aperture configured for filtered air to exit said housing.

* * * * *